(12) United States Patent
Lee

(10) Patent No.: US 7,367,550 B2
(45) Date of Patent: May 6, 2008

(54) PERISTALTIC MIXING AND OXYGENATION SYSTEM

(75) Inventor: Harry Lee, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 575 days.

(21) Appl. No.: 10/717,409

(22) Filed: Nov. 18, 2003

(65) Prior Publication Data

US 2005/0106045 A1    May 19, 2005

(51) Int. Cl.
*B01F 3/04* (2006.01)
(52) U.S. Cl. .............. 261/81; 261/104; 261/122.1
(58) Field of Classification Search ............ 261/81, 261/102, 104, 105, 121.1, 122.1, 122.2, 124
See application file for complete search history.

(56) References Cited

U.S. PATENT DOCUMENTS

| | | | | |
|---|---|---|---|---|
| 4,029,581 A | * | 6/1977 | Clough et al. | 210/220 |
| 4,512,933 A | * | 4/1985 | Harden | 261/30 |
| 4,684,486 A | * | 8/1987 | Ricchio | 261/36.1 |
| 4,793,714 A | * | 12/1988 | Gruber | 366/150.1 |
| 5,081,035 A | * | 1/1992 | Halberstadt et al. | 435/297.4 |
| 5,510,166 A | * | 4/1996 | Inoue et al. | 428/76 |
| 5,769,993 A | * | 6/1998 | Baldauf | 156/164 |
| 6,039,309 A | * | 3/2000 | Kuklinski | 261/1 |
| 6,267,837 B1 | * | 7/2001 | Mitchell et al. | 156/209 |

* cited by examiner

*Primary Examiner*—Scott Bushey
(74) *Attorney, Agent, or Firm*—Stacy L. Blasberg; Chooate Hall & Stewart LLP

(57) ABSTRACT

The present invention provides devices and methods for achieving mixing and gas exchange in chambers having a small volume. According to the invention a chamber includes one or more walls that are made of a gas-permeable material and that include multiple portions that are selectively deflectable into the interior of the chamber. The deflectable portions are in communication with a hollow cavity or space that can be pressurized. Pressurization results in deflection of the deflectable portion into the chamber. Pressurization is achieved using a gas or fluid that contains a gas of interest such as oxygen. The portions are deflected in a sequence that results in peristaltic action that mixes and oxygenates the contents of the chamber. In a preferred embodiment of the invention the hollow cavities are an assembly of tubes that deflect into a plurality of chambers. A particular use for the invention is as a culture vessel for cells such as bacteria.

111 Claims, 19 Drawing Sheets

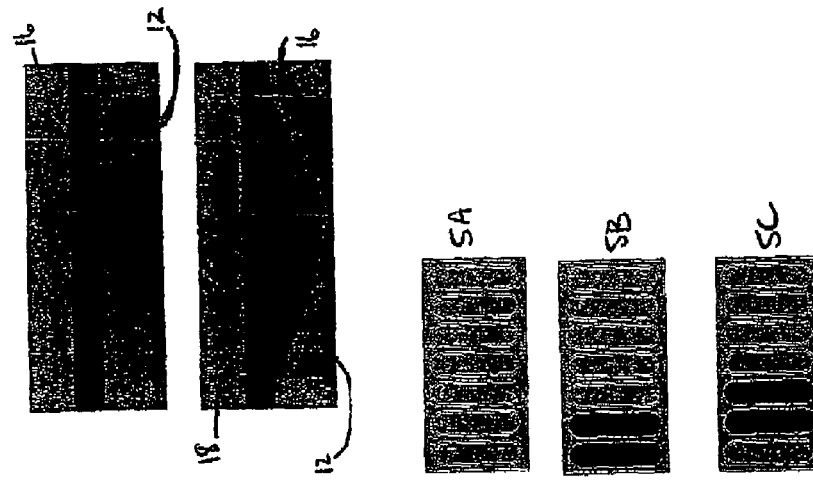
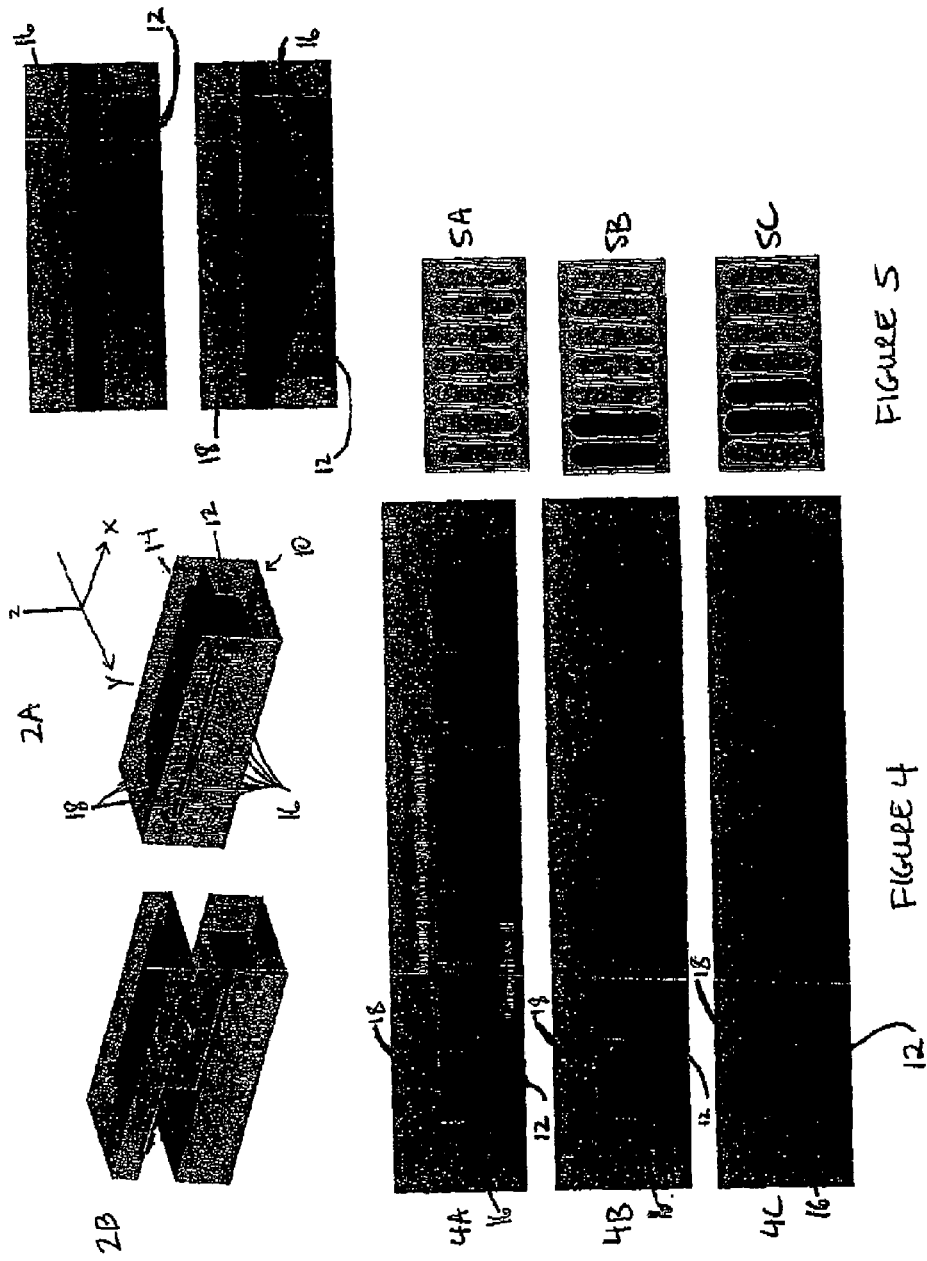

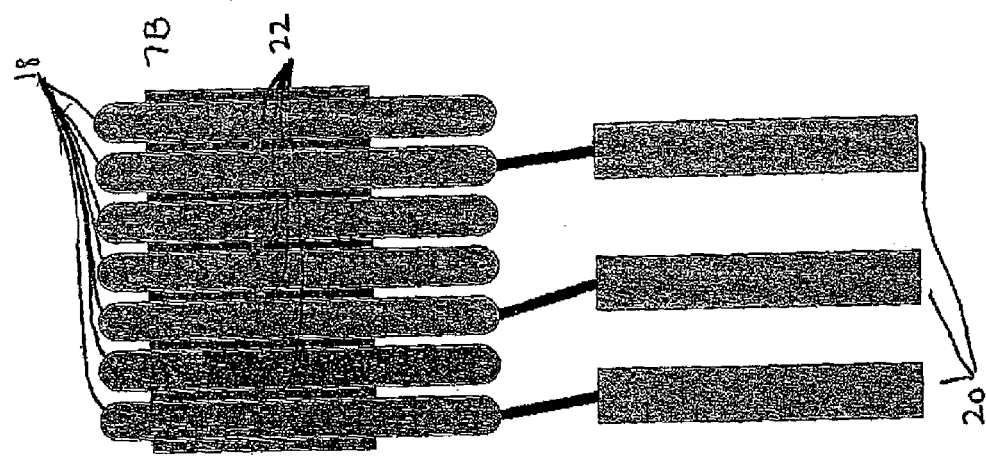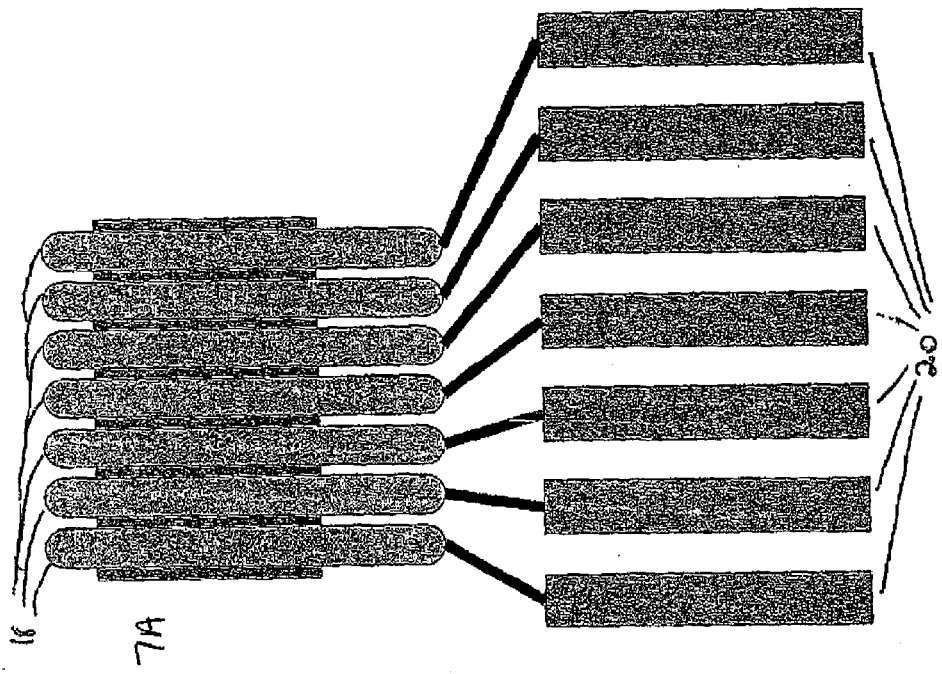
FIGURE 7

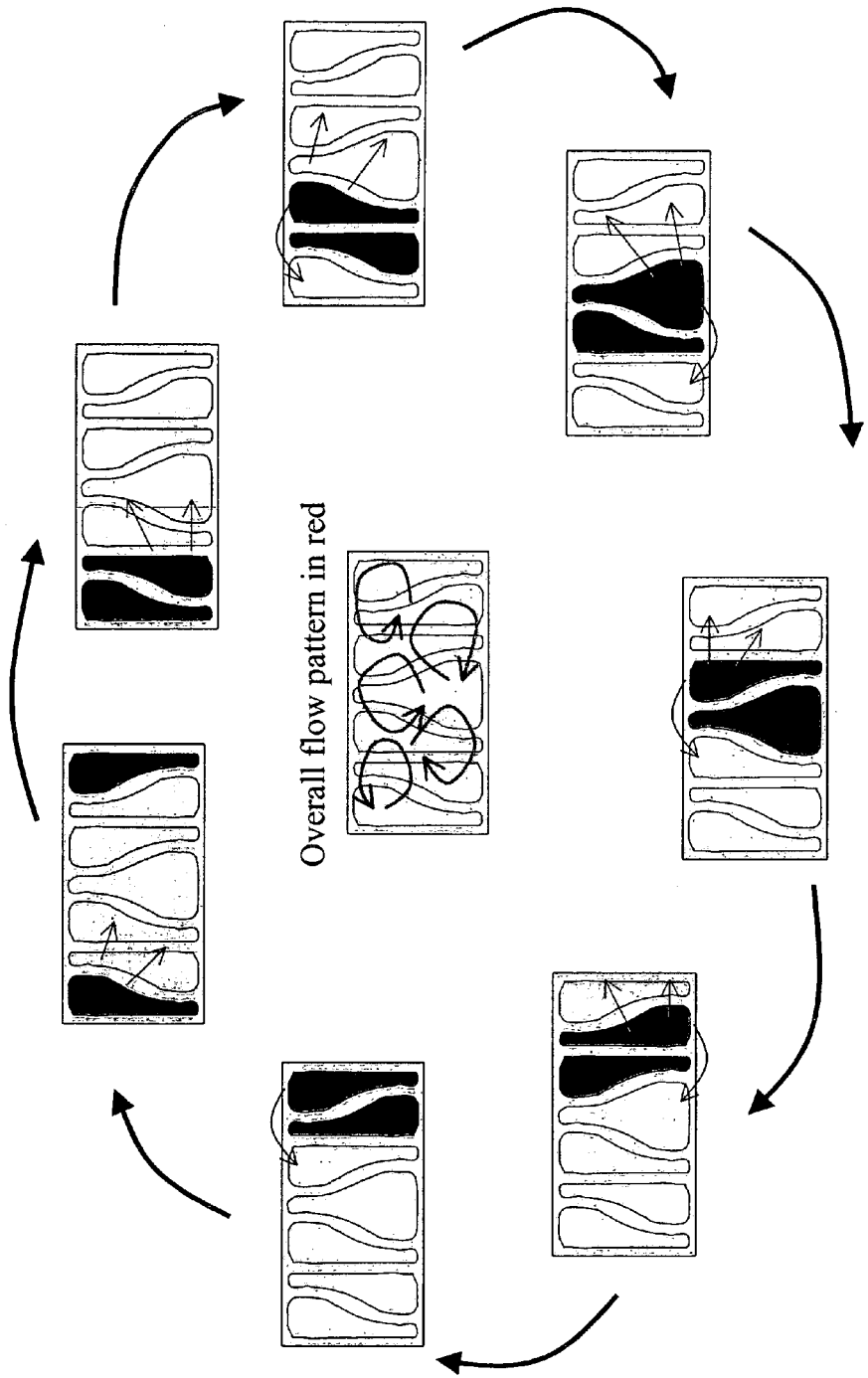

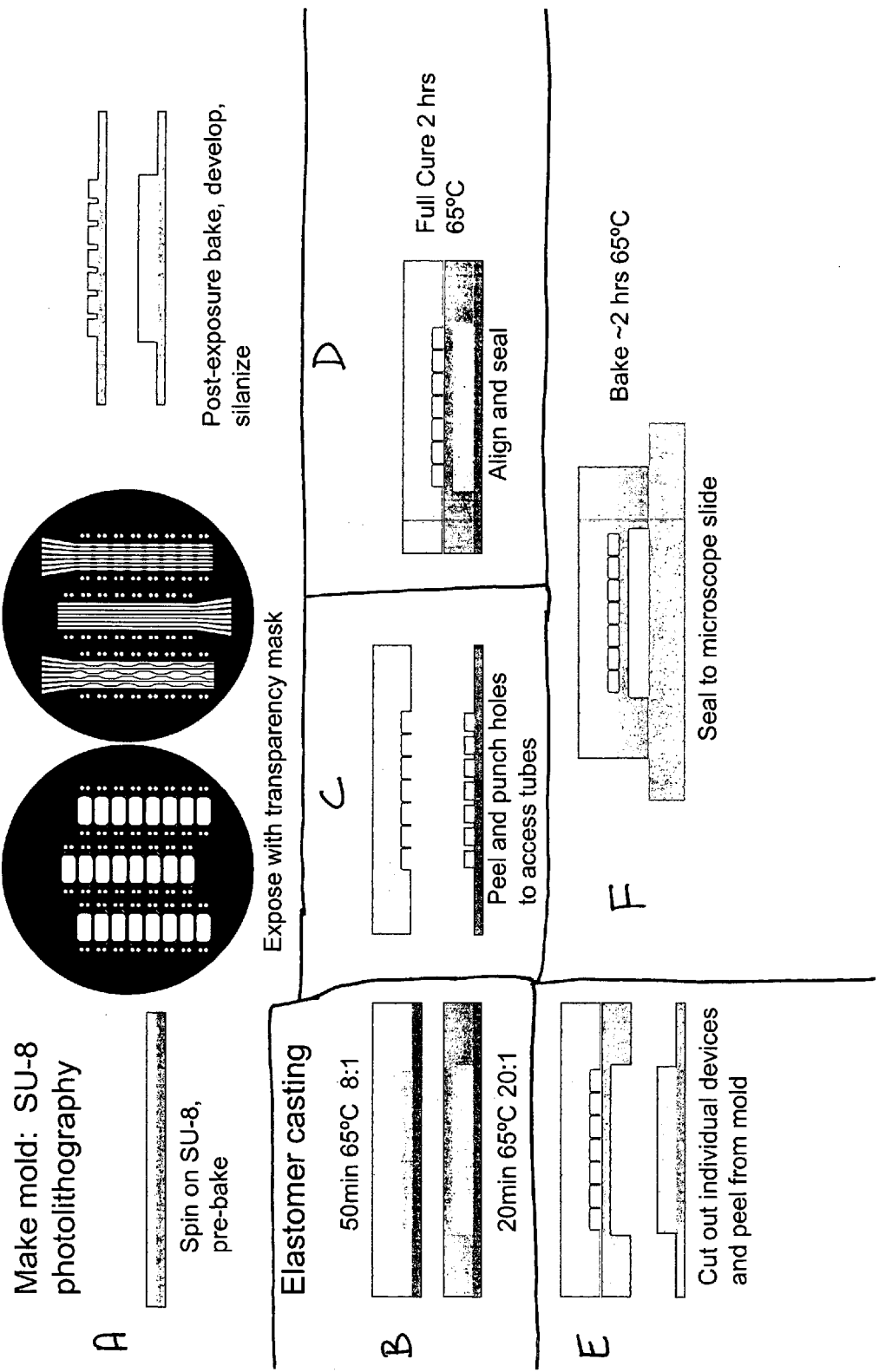

FIGURE 11

Another variation:

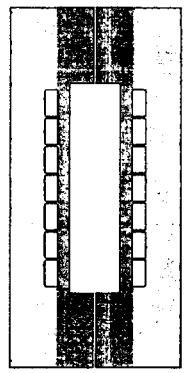
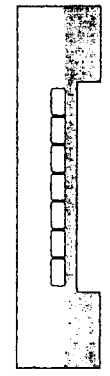

Cut out individual devices and peel from mold

Seal two together back to back for double sized chamber.

FIGURE 12

Another embodiment

Thin 100-300um thick PDMS membrane spin on and peel off

Same elastomer molded tubes, or etched glass tubes, or laser machined tubes in plastic Conventionally machined wells, or injection molded wells, or epoxy molded wells, or elatomer molded wells.

FIGURE 18
FIGURE 19
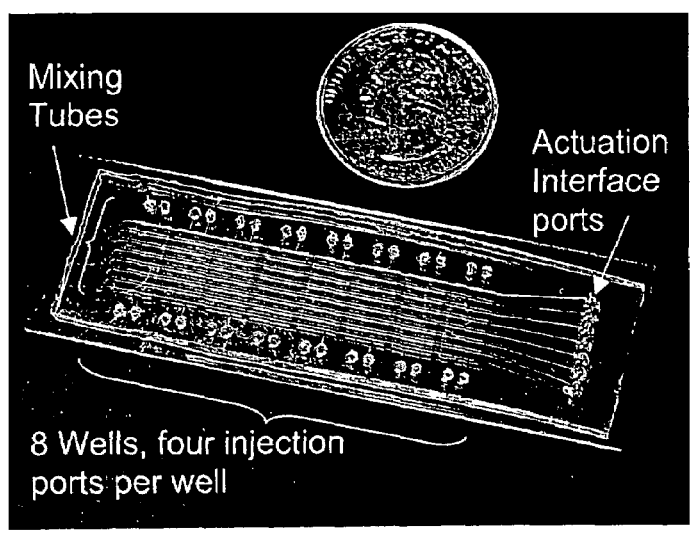
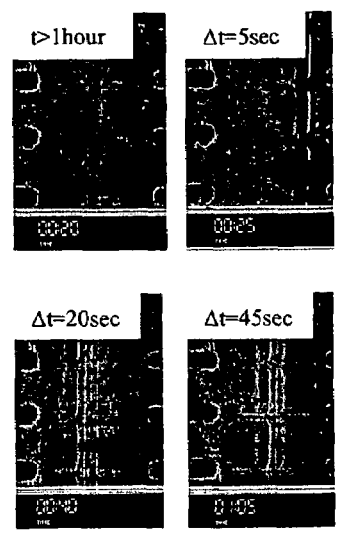
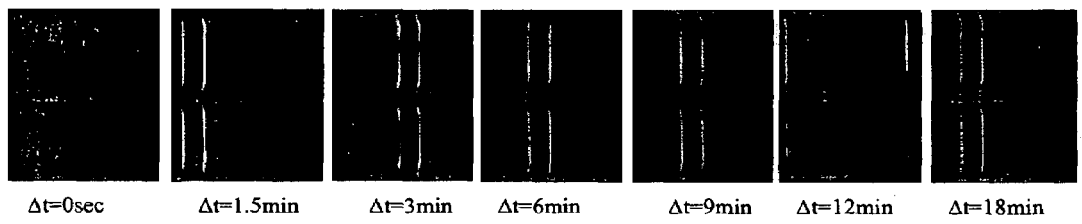
FIGURE 20

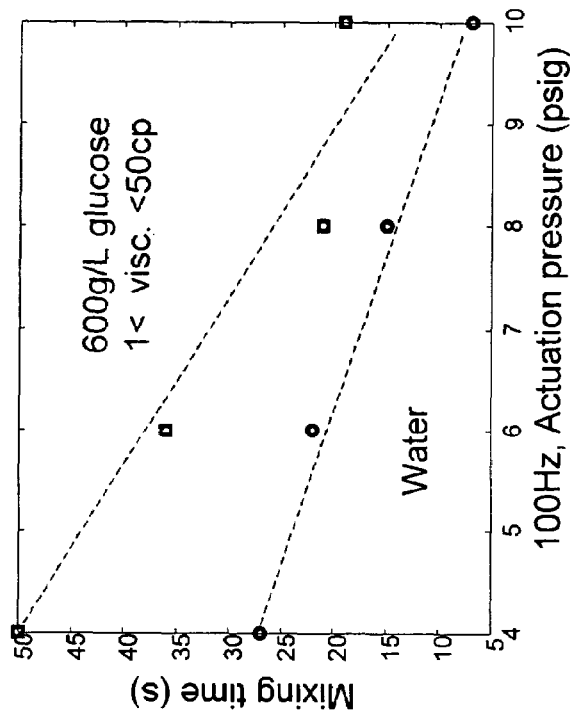
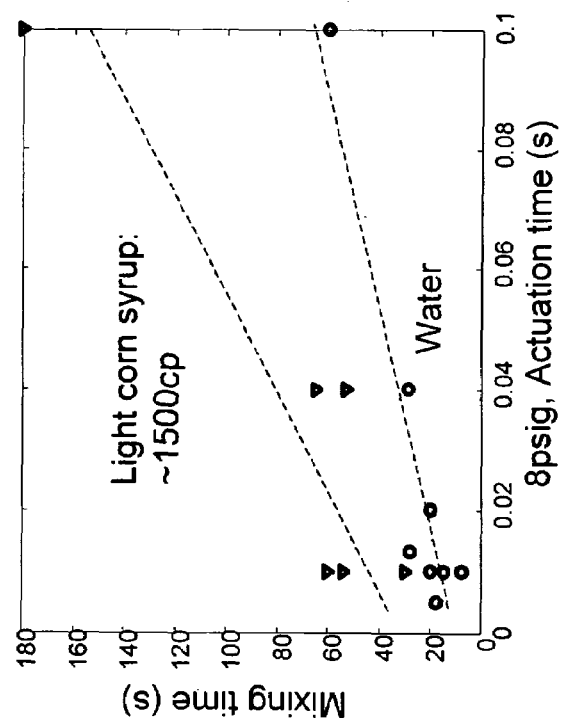
FIGURE 24

PERISTALTIC MIXING AND OXYGENATION SYSTEM

BACKGROUND OF THE INVENTION

A large number of useful substances are most efficiently produced by microorganisms such as bacteria or fungi (Shuler, M. L. and Kargi, R., *Bioprocess Fundamentals* (2$^{nd}$ Ed.), Prentice Hall (2001); Doran, P., *Bioprocess Engineering Principles*, Academic Press (1995)). This includes some pharmaceutical products, food additives and supplements, bulk chemicals such as ethanol, and enzymes. While organisms that produce the desired substance may occur in nature, their metabolism is likely not optimized to produce the desired product, and harvesting product from microorganisms as they exist in nature is frequently not practical. In addition, an increasing number of useful products including a variety of pharmaceutical agents (e.g., antibodies, enzymes) are produced by harvesting them from mammalian cells or culture medium. Bioprocess development typically involves improving the microorganism or cell (e.g., through selection, mutation, or recombinant DNA technology) and/or engineering its environment to produce the desired product with high efficiency.

Developing efficient and practical bioprocesses frequently involves testing a large number of different strains and environmental conditions in various combinations. Although the ultimate goal is to identify an appropriate strain and conditions for production on an industrial scale (e.g., in a bioreactor with a 100,000-300,000 liter volume), bioprocess development begins on a much smaller scale. For example, screening of different strains is often conducted in microtiter plates, under relatively uncontrolled conditions and with only limited possibility of monitoring conditions during culture. After identification of strains that appear promising, further screening is performed in shaking flasks with a much larger volume (e.g., 25-100 ml). Such flasks typically allow only partial control over important environmental variables and cannot achieve the high oxygen ($O_2$) concentrations typically used in large-scale fermentation processes. Thus the usefulness of these open loop systems for selecting the organisms that will be optimal under actual bioprocess conditions is limited.

Scale-up to bench-scale, closed loop bioreactors, which offer improved control over environmental variables, increased oxygenation, and therefore the ability to achieve higher cell densities, is the next step. However, bench-scale bioreactors, with typical volumes of between 0.5 and 10 liters suffer from a number of drawbacks. Because of their large size, relatively high cost, and the time and effort required to obtain the data it is typically not practical to test as many combinations of strains and environmental conditions as would be desirable.

The inventors have recognized that there is a large technology gap between microtiter plates/flasks and closed loop controlled bioreactors. This gap is important because its presence may allow potentially productive strains to be eliminated at the microtiter plate or shake-flask screening stage, due to optimization with respect to uncontrolled physical parameters, or it may allow potentially non-productive strains that do not perform well under typical industrial scale bioprocess conditions, e.g., high cell densities, to proceed to the next stage. There is thus a need in the art for a system to fill this gap. In particular, there is a need for small scale bioreactor systems that allow multiple experiments to be performed in parallel without an accompanying increase in cost and that offer improved control over environmental parameters. However, in order to realize such a system, a number of challenges need to be overcome. One of these challenges is to develop a system that can provide effective mixing and oxygenation in a small volume.

SUMMARY OF THE INVENTION

The present invention addresses this need, among others. In one aspect, the invention provides a device for fluid mixing and gas exchange comprising a housing defining a chamber for holding a liquid, wherein a wall of the chamber comprises a plurality of gas-permeable portions, and wherein the gas-permeable portions are selectively deflectable into the interior of the chamber. In certain embodiments of the invention the portions are deflectable by pressurizing a cavity in communication with the deflectable portion. In general, the cavities are pressurized using a gas or liquid having a higher concentration of a gas of interest (e.g., oxygen) than that in the chamber, e.g., from a high pressure reservoir. Pressurization of the cavities results in deflection of the deflectable portions into the chamber, thereby forcing the liquid inside to move and typically also pushes up the undeflected deflectable portions of the wall. In certain preferred embodiments of the invention the gas-permeable portions are deflected in a repetitive sequence that mixes and oxygenates the contents of the chamber by peristaltic action. In certain embodiments of the invention the device is fabricated as layers of an elastomeric structure. In other embodiments of the invention at least part of the housing is fabricated from glass, plastic, or metal, and a gas-permeable membrane forms the wall of the chamber having the deflectable portions. In certain embodiments of the invention multichamber devices are provided, in which each cavity contributes to the mixing and oxygenation of multiple chambers.

In another aspect, the invention provides a device comprising a set of blind-ended tubes (e.g., blind at at least one end but having at least one connection to a high pressure source) made at least in part of a gas-permeable material, wherein the tubes form portions of a wall of a chamber, and wherein the portions of the wall are selectively deflectable into the interior of the chamber. In another embodiment, the invention provides a device comprising a set of blind-ended tubes (e.g., blind at at least one end but having at least one connection to a high pressure source) made at least in part of a gas-permeable material, wherein the tubes are separated from the interior of a chamber by a layer of gas-permeable material that forms a wall of the chamber, wherein the tubes are selectively pressurizable wherein pressurization of the tubes causes portions of the wall to deflect into the interior of the chamber. In another embodiment, the invention provides a device comprising a set of tubes made at least in part of a gas-permeable material, wherein the tubes are separated from the interior of a chamber by a later of gas-permeable material that forms a wall of the chamber, wherein pressurization of the tubes causes portions of the wall to deflect into the interior of the chamber, and wherein the tubes are pressurized from one end and are opened or closed on the other end to allow gas to flow through or to pressurize the tube, respectively.

The invention further provides a method of achieving mixing and gas exchange of a volume of liquid comprising the steps of: (i) introducing a liquid into the chamber of a device comprising a housing defining a chamber for holding a liquid, wherein a wall of the chamber comprises a plurality of gas-permeable portions, and wherein the gas-permeable portions are selectively deflectable into the interior of the chamber and (ii) actuating the device so as to repetitively deflect the deflectable gas-permeable portions into the chamber.

In another aspect, the invention provides a method of culturing cells comprising: steps of (i) introducing cells and a liquid cell culture medium into the chamber of a device comrpising a housing defining a chamber for holding a liquid, wherein a wall of the chamber comprises a plurality of gas-permeable portions, and wherein the gas-permeable portions are selectively deflectable into the interior of the chamber and (ii) actuating the device so as to repetitively deflect the deflectable gas-permeable portions into the chamber.

In another aspect, the invention provides a method of making a device for fluid mixing and gas exchange comprising steps of: (i) fabricating a first layer defining a chamber; (ii) fabricating a second layer defining a plurality of cavities; (iii) fabricating a third layer comprising a gas-permeable material; and (iv) bonding the layers so that the third layer is interposed between the first and second layers so as to separate the chamber from the cavities and comprises portions that are selectively deflectable into the chamber upon pressurization of the cavities.

The peristaltic mixing and oxygenation devices of the invention find use in bioprocess development as well as in a variety of other applications in addition to bioprocess development. They may be used in any situation in which mixing and/or gas exchange in a small volume is desired including, but not limited to, the development of more efficient chemical reactions of any type. For example, different reactants, catalysts, and environmental conditions such as temperature can be tested in parallel.

This application refers to various patents and publications. The contents of all of these are incorporated by reference. In addition, the following publications are incorporated herein by reference: Stephanopolous, G., ed. *Bioprocessing*. Second ed. *Biotechnology*, H.-J. Rehm, et al. (eds) Vol. 3. 1993, VCH Publishers Inc.: New York; Bailey, J. E. and D. F. Ollis, *Biochemical Engineering Fundamentals*. Second ed. McGraw-Hill chemical engineering series. 1986: McGraw-Hill, Inc.; Mulder, M., *Basic Principles of Membrane Technology*. Second ed. 1996: Kluwer Academic Publishers.

BRIEF DESCRIPTION OF THE DRAWING

FIG. 2A shows a perspective view of a chamber with a plurality of selectively deflectable portions along the top wall of the chamber.

FIG. 2B shows an exploded view of the chamber of FIG. 2A.

FIG. 3 shows a schematic cross-sectional view of a deflectable portion both prior to and following deflection.

FIGS. 4A-4C show an enlarged view of the chamber and an actuation sequence of the deflectable portions to achieve peristaltic action.

FIGS. 5A-5C show a top view of the deflection pattern in the unactuated state (FIG. 5A) and the first two actuated states.

FIGS. 7A and 7B show alternate actuation mechanisms. In FIG. 7A each cavity is connected to a valve which is in turn connected to a high pressure reservoir. In FIG. 7B the cavities comprise 3 groups, each of which is selectively deflectable. Cavities in each group are interconnected via a narrow hollow region.

FIG. 8 shows a schematic of a top view of an embodiment of the invention in which the width of the deflectable portions is variable and in which the portions do not all have identical shapes. Adjacent portions contain complementary convex and concave regions.

FIG. 10 presents an overview of a multilayer soft lithography fabrication process that was used to implement a device of the invention.

FIG. 11 shows an alternative embodiment of the invention in which two devices are sealed back to back to form a device in which two walls comprise selectably deflectable portions.

FIG. 12 shows an embodiment of the invention in which a layer defining cavities is fabricated either using an elastomer or from a material such as glass, plastic, or metal.

FIG. 18 shows an enlarged view of a device of the invention in which the actuation interface ports and injection ports are visible.

FIG. 19 presents a sequence of images showing the progress of mixing in a device with straight-sided deflectable portions.

FIG. 20 shows a sequence of images showing the progress of mixing Columbo™ yogurt and dye in a device with straight-sided deflectable portions.

FIG. 24A shows mixing time trends over a range of actuation times for water and water with glucose (600 g/L).

FIG. 24B shows mixing time trends over a range of actuation pressures for water and light corn syrup.

DETAILED DESCRIPTION OF CERTAIN PREFERRED EMBODIMENTS OF THE INVENTION

I. Overview

Development of small scale bioreactors must take a number of considerations into account. In general, the minimum size of conventional bioreactors is related to the desire for modularity that can be achieved by using industry standard dissolved oxygen and pH probes, which are typically 0.5 inches in diameter and 6-8 inches long, and industry standard mixing technology to support oxygenation. This typically requires growth chambers large enough to support high Reynolds number turbulent flows and electric motors with adequate torque at high angular velocity. In general, the Reynolds number of a fluid flow describes its flow regime, e.g., laminar or turbulent flow (Beebe, D. J., Mensing, G. A., and Walker, G. M., "Physics and applications of microfluidics in biology", *Annu. Rev. Biomed. Eng.*, 4:261-86.). Turbulent flow is chaotic and unpredictable (i.e., it is generally not possible to predict the position of a particle in the fluid stream as a function of time), in contrast with laminar flow in which the velocity of a particle in a fluid stream is not a random function of time.

While technologies such as fluorescence based pH and dissolved oxygen sensors exist that can be used to address the desire to monitor conditions within the growth chamber, the issues that must be addressed to achieve desirable levels of oxygenation and mixing are more challenging. At small length scales oxygen transport occurs by diffusion, i.e., the process by which a concentrated group of particles in a volume spreads out over time by Brownian motion, so that the average concentration of particles within the volume becomes constant. Diffusion is the major process by which oxygen is transferred from gas bubbles to cells. In conventional stirred tank bioreactors, sparging and mixing disperse small gas bubbles that move rapidly throughout the fluid volume, thereby minimizing the effective distance between an oxygen rich bubble surface and the cells.

Figure 1:
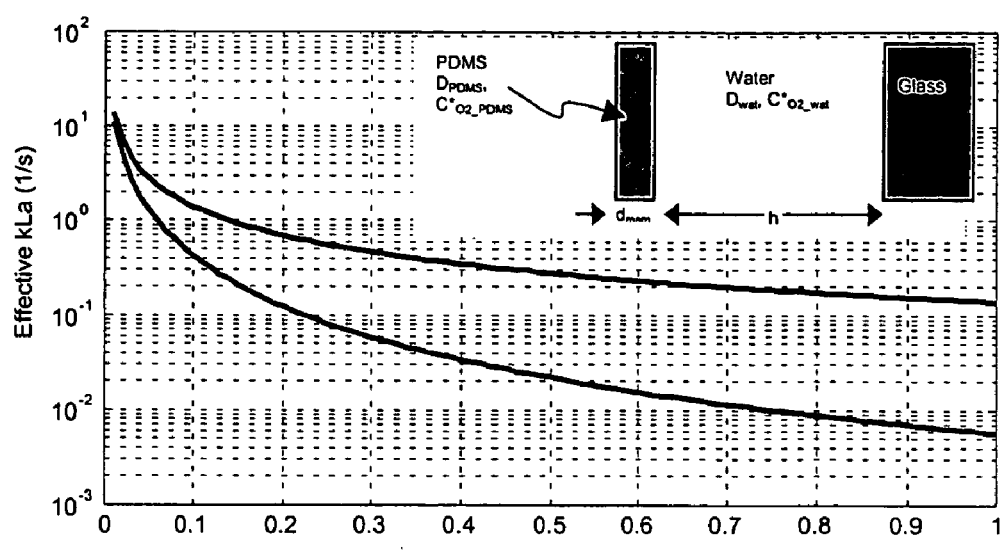
FIG. 1 is a plot showing calculated effective $k_{La}$ (mass transfer coefficient) values for $O_2$ for a thin layer of water covered by a PDMS membrane. The inset illustrates a one dimensional model of a thin bioreactor growth chamber.

In small volumes, it is more difficult to generate turbulent flows to disperse bubbles at sufficient velocity to achieve efficient oxygenation. However, if the maximum distance between the cells and an oxygen rich surface can be constrained to a sufficiently small value, efficient oxygenation can be achieved (A. Zanzotto, N. Szita, M. A. Schmidt, K. F. Jensen, "Microfermentors for the rapid screening and analysis of biochemical processes," 2nd Annual International IEEE EMBS Special Topic Conference on Microtechnologies in Medicine and Biology, pp. 164-168, 2002.). For example, the geometry shown in FIG. 1, in which a thin polydimethylsiloxane (PDMS) membrane, which acts as a sterile barrier and has a high oxygen permeability, covers a thin growth well, the maximum distance between a cell (e.g., a bacterium), is simply the thickness of the growth well. While using a gas-permeable membrane as one wall of a growth chamber can provide enhanced oxygenation over a limited distance, the inventor has recognized that fluid mixing would improve the oxygenation capability still further. FIG. 1 shows the results of an analysis using a steady state one dimensional diffusion model, in which the calculated effective $k_L a$ values for the mixed case (upper curve) are given by:

$$k_L a_{\mathit{eff\_mixed}} = D_p/(K \cdot d_{mem} \cdot h) \quad \text{(Eq. 1)}$$

and for the unmixed case (lower curve) by:

$$k_L a_{\mathit{eff\_mixed}} = 1/[h^2/(3\,D_w) + K \cdot d_{mem} \cdot h/D_p] = 1/[1/k_L a_{\mathit{eff\_mixed}}] \quad \text{(Eq. 2)}$$

where h is the height of the growth chamber, $d_{mem}$ is the thickness of the PDMS membrane, K is the partition coefficient ($C_{sat\_water}/C_{sat\_PDMS}$), $D_p$ is the diffusion coefficient of $O_2$ PDMS, and $D_w$ is the diffusion coefficient of $O_2$ in water.

Although numerical values would be different under actual growth conditions (e.g., in cell culture medium, etc.) these calculations demonstrate the importance of minimizing the thickness of the fluid layer and the significant contribution of mixing to oxygenation. The minimum thickness will generally be determined by the constraints presented by the desired volume and the maximum total area of each growth chamber. In general, thicker wells with smaller volumes as opposed to wells with large surface area to volume ratios are desirable from the standpoint of maintaining culture homogeneity. While not wishing to be bound by any theory, the calculations shown in FIG. 1 suggest that mixing will be needed to achieve an effective $k_L a > 0.2/s$ for growth chamber heights larger than approximately 150 μm.

In addition, mixing can be essential for pH control and/or substrate feed since any fluid addition is typically local, and mixing is necessary to rapidly smooth any concentration inhomogeneities. For example, if a droplet of aqueous base is introduced at one wall of a growth chamber with dimensions 10×5×0.5 mm, assuming a diffusivity for NaOH of $D^{NaOH} = 10^{-5}$ cm$^2$/s (J. A. Wesselingh, R. Krishna, Mass. transfer in multicomponent mixtures, Delft University Press, Delft: p. 131, 2000.), the time necessary to distribute the base to achieve a uniformity within 1% throughout the chamber is given by $0.6\,L^2/D_{NaOH} = 16$ hours. Similar results would be obtained in the case of a nutrient or other substrate such as glucose. It is evident that response times on the order of 10 hours are highly suboptimal, thus attempts at pH or substrate control based on diffusion would likely require a method that would allow distribution of the control fluid over a large volume or cross-sectional area. Mixing in small volumes has long been a challenge in the microfluidics community. In general, the fluid regime that microfluidic devices occupy is characterized by laminar flows in which two fluids remain separated until mixed by diffusion (Beebe, D. J., Mensing, G. A., and Walker, G. M., "Physics and applications of microfluidics in biology", *Annu. Rev. Biomed. Eng.*, 4:261-86.). Therefore, rapid mixing is notoriously difficult to achieve because the interfacial area is small. Mixing of large particles, such as cells, can be particularly problematic, which is a concern for bioprocess applications in which it is frequently desirable to avoid cell aggregation or accumulation, e.g., on the bottom of the growth chamber.

A number of efforts have been made to address the need for mixing in small scale, e.g., microfluidic, devices. Passive mixers typically use channel geometry to increase the area over which diffusion can occur. Examples include a distributive mixer (Bessoth, F., et al., *Anal. Commun.*, 36:213-215,1999; Koch, M., et al., *J. Micromech. Microeng.* 8:123-26, 1998; Hinsmann, P., et al., *Lab Chip* 1: 16-21, 2001), a static mixer (Schwesinger, N., et al., *J. Micromech. Microeng.*, 6:99-102, 1996; Bertsch, A., et al., *Lab Chip* 1:56-60,2001), a T-type mixer (Bokenkamp, D., et al., *Anal. Chem.* 70:232-36, 1998), and a vortex mixer. Active mixers use external sources to increase the interfacial area between fluid streams. Examples include a PZT (lead-zirconate-titanate)-based mixer (Yang, Z., et al., *Electrophoresis,*

21:116-19), electrokinetic mixers (Oddy, M., et al., *Anal. Chem.,* 73:5822-32, 2001), a chaotic advection mixer (Evans, J., et al., *Planar laminar mixer.* Presented at Annu. Workshop Micro Electro Mech. Syst., 10$^{th}$, Nagoya, 1997), magnetically driven mixers, etc. (See also M. Yi, H. H. Bau, H. Hu, Micro Electro Mechanical Systems MEMS 2000 ASME International Mechanical Engineering Congress and Exposition. 2000: pp. 367-74.) Active mixing by means of pumps, e.g., microfabricated pumps, is also being explored (Chou, H—P., et al., *Biomedical Microdevices,* 3:4, 323-330,2001).

II. Features and Operation of the Device

The present invention offers a new approach to addressing the challenges of both mixing and gas exchange in a small chamber. The invention is useful for aiding gas transport and for mixing fluids with a wide range of viscosities. According to the invention one or more walls of a chamber located within a housing includes a plurality of selectively deflectable portions made of a gas-permeable material. The gas-permeable portions allow for the exchange of gases between the chamber and a hollow space outside the chamber, which is separated from the chamber by the gas-permeable material of which these portions of the wall are fabricated. By deflecting the portions into the interior of the chamber, e.g., in any of a variety of preselected sequences, peristaltic action is achieved, resulting in mixing of the contents of the chamber. Without intending to limit the invention in any manner, for purposes of description a peristaltic wave may in general be defined as a progessive wave of area expansion or contraction propagating along the length of a flexible boundary (Selverov and ref therein).

The present invention provides a housing that defines a chamber, wherein at least one wall of the chamber comprises a plurality of selectively deflectable portions. The housing may be mounted on a substrate, e.g., a solid support such as glass, metal, plastic, etc., which may form the bottom of the chamber. In preferred embodiments, the invention achieves an approximation to peristalsis by sequentially deflecting portions of a wall of a chamber (or portions of multiple walls) into the chamber. By "wall" is meant any surface that separates the interior of a chamber or well from the exterior, e.g., the top, bottom, or any side of a chamber or well. By "selectively deflectable" is meant that a fraction of the total deflectable area, e.g., a subset (one or more) of the portions can be deflected into the chamber without deflecting the remainder of the total deflectable area (i.e., the remaining portions). In general, the deflectable portions are formed by constraining a gas-permeable portion of the wall so that it does not move along its perimeter with respect to the interior of the chamber, while the remainder of the portion, within the perimeter, is able to move.

In a chamber with a wall containing gas-permeable portions (or made entirely of a gas-permeable material), the gas can diffuse across the wall much as depicted in FIG. 1, thereby increasing the concentration of the gas in the chamber. Deflection of the deflectable portions displaces the contents of the chamber in the volume region into which the portions deflect, forcing them to move elsewhere in the chamber. This displacment results in fluid flow, which mixes the contents of the chamber and brings a larger fraction of the contents into contact with the oxygen-rich surface of the gas-permeable portions of the wall. In addition, in preferred embodiments of the invention deflection of the deflectable portions increases the gas-permeable surface area in contact with the contents of the chamber as described in further detail below. Furthermore, when deflection is achieved by pressurizing a hollow space or tube adjacent to the wall (see below), $O_2$ diffusion is increased relative to the undeflected case since the increased pressure drives more $O_2$ into the wall and into the contents of the chamber.

According to certain embodiments of the invention the exterior surface of the deflectable portions, i.e., the surface that is not in contact with the contents of the chamber, is in communication with (i.e., in contact with) a hollow space containing a gas or fluid having at least as great a concentration of a gas of interest as the concentration which it is desired to achieve or maintain within the chamber. Typically the hollow space is in communication with a reservoir (e.g., a high pressure reservoir) which contains the gas of interest. The reservoir may serve both as a supply of the gas of interest and as a source of pressure to achieve deflection of the gas-permeable portions as described in further detail below. In certain embodiments of the invention the reservoir is humidified and/or warmed or cooled. For purposes of description herein, it will be assumed that the gas of interest is $O_2$, although the invention may be employed to increase the concentration of any gas of interest within the chamber by selection of a material that is permeable.

FIGS. 2A and 2B depict an exemplary embodiment of a device 10 for fluid mixing and gas exchange in accordance with the invention. FIG. 2A is a perspective view showing a chamber 12 which may also be referred to as a "well" or "growth well" herein, located within housing 14. The device may be placed on a substrate, e.g., a planar substrate such as a glass slide. FIG. 2B shows an exploded view of the device, in which the interior of the chamber is visible. While the chamber depicted in FIG. 2 is rectangular in cross section in the xy, xz, and yz planes, it will be appreciated that any of a large number of different chamber geometries may be used. For purposes of description herein, and in reference to a particular embodiment of the invention that has been constructed and tested (see below), it will be assumed that the chamber is rectangular in cross section as shown in FIG. 2. However, it is to be understood that the chamber may assume other geometries, e.g., cubical, cylindrical, conical. Typically the length of the chamber in the z direction will be less than its length in the x and y directions.

In general, the dimensions and volume of the chamber can vary. In certain embodiments of the invention the total chamber volume is at least 0.5 µl, e.g., 0.5 µl to 10 µl, 10 µl-50 µl, 50-150 µl, 150-500 µl, 500 µl-1 ml, or 1-2 ml, inclusive. Other ranges, including values greater than 2 ml, are also withint the scope of the invention. In various embodiments of the invention the ratio of the area of the chamber wall (or walls) that includes the deflectable portions to the total volume of the chamber, referred to herein as the surface area to volume ratio, is at least 50/m, e.g., 50/m-20,000/m; 100/m-10,000/m; 500/m-5000/m; 500/m-1000/m; 1000/m-5000/m. For example, a chamber in which the wall comprising the deflectable portions has dimensions 10 mm×5 mm and in which the depth of the chamber is 2 mm has a surface area to volume ratio of 500/m. Other ranges are also within the scope of the invention. Exemplary non-limiting values for the dimensions of the wall comprising the deflectable portions are, for example, 5 mm×10 mm, 10 mm×20 mm, 20 mm×30 mm, etc. Exemplary non-limiting values for the depth of a chamber are: 50 um, 100 um, 500 um, 1 mm, etc. Thus in certain embodiments of the invention the device is a microscale device, by which is meant a device in which at least one dimension (e.g., a dimension of the chamber or of a deflectable portion of a chamber wall) is below 1000 µm and in which preferably variation in at least one dimension of the structure is controlled to the micron level. In other embodiments of the invention the device is a macroscale device, i.e., a device that does not meet these limitations.

The top wall of the chamber in FIG. 2 comprises 7 deflectable portions 16, in both FIGS. 2A and 2B. The deflectable portions extend in the −y direction through the width of the chamber in the y dimension. FIGS. 2A and 2B also depict a hollow space 18, located adjacent to and in contact with each deflectable portion. In FIGS. 2A and 2B, hollow spaces 18 extend in the −y direction through the width of the chamber in the y dimension. However, in general, a hollow space 18 need not extend through the entire width of a chamber and need not contact the entire corresponding deflectable portion. In certain embodiments of the invention hollow spaces 18 form an integral part of the wall of the chamber that comprises the deflectable portions. Thus the deflectable portions of the chamber wall also form part or all of the wall of the hollow space where it adjoins the chamber. Thus the hollow space is in contact with the deflectable portion since the deflectable portion provides part or all of the wall of the hollow space. In other embodiments of the invention hollow spaces 18 are external to the wall that comprises the deflectable portions. It will be appreciated that in the latter case the hollow spaces should be fabricated in a material that is permeable to the gas of interest, so that the gas may diffuse from the hollow spaces into the deflectable portions of the wall. The deflectable portions themselves may be individual, i.e., physically separated from each other by a intervening region, which may be made from a different material. Alternately, the deflectable portions may be part of a single layer or membrane, which forms the wall of the chamber. Individual portions of the layer or membrane are selectively deflectable, e.g., by virtue of their contact with individual hollow spaces that can be selectively pressurized as described below.

According to the invention hollow spaces 18 are filled with a gas or fluid that contains the gas of interest, e.g., $O_2$. For example, a hollow space 18 may contain room air, an $O_2$-rich gas (e.g., a gas containing a higher concentration of $O_2$ than present in room air at standard temperature and pressure), a liquid such as a perfluorocarbon containing a high concentration of $O_2$, etc. In certain preferred embodiments of the invention hollow space 18 are in communication with a high pressure reservoir (e.g., a reservoir having a higher pressure than that within the chamber) and/or with other means of pressurizing the hollow space. In general, the high pressure reservoir may serve both as a source of high pressure and as a source of the $O_2$-containing gas.

In general, the hollow space is enclosed so that increasing the pressure therein results in deflection of deflectable portion 16 into the chamber. When actuated, e.g., by pressurization of the overlying hollow space, the portions deflect in the −z direction, into the interior of the chamber. According to the invention the portions are deflected in a sequence, e.g., from left to right (in the +x direction), either individually or in groups, to mix and oxygenate the contents of the chamber.

As discussed further below, hollow spaces 18 may assume the form of tubes. In those embodiments of the invention in which the hollow spaces are in the form of tubes, the tubes may be blind at one end and connected to a high pressure reservoir at the other end (or blind at both ends and connected elsewhere to a high pressure reservoir), or may be blind at both ends and interconnected with one or more adjacent tubes, or may be connected to a high pressure reservoir at one end and a valve at the other end (which in turn communicates with the atmosphere of a low pressure reservoir), etc., so that when the valve is closed the tube is pressurized, and when the valve is open gas flows through the tube and the tube is depressurized.

FIG. 3 shows a schematic cross-sectional view of a deflectable portion 16 and a chamber 12. Hollow space 18, overlies the deflectable portion. The upper portion of FIG. 3 shows the unactuated (low pressure) state in which the portion is not deflected. The lower portion of the figure shows the actuated (high pressure) state in which the portion is deflected into the chamber except at the perimeter, which is constrained. In an actual device, the chamber would extend in the left and right directions, and the top would comprise additional deflectable portion(s). FIG. 3 shows an embodiment of the device that is constructed in layers in which adjacent deflectable portions are physically joined and adjacent hollow spaces are located within a continuous layer of material. While pressurization of the cavity is a preferred means of causing deflection, other deflection methods can also be used.

In preferred embodiments of the invention one or more walls of the chamber includes at least 3 deflectable portions in order that peristaltic action can be achieved. The number of deflectable portions will vary, e.g., depending on the chamber volume and the surface area of the wall. Embodiments with 4, 5, 6, 7, 8, 9, or 10 deflectable portions are encompassed as are embodiments with greater than 10 deflectable portions. In certain embodiments of the invention the number of deflectable portions is between 6 and 10, inclusive. In general, individual deflectable portions are spaced apart, i.e., they are separated by a nondeflectable region. In certain embodiments of the invention the total area of the deflectable portions constitutes at least 10% of the area of the wall that includes them. In other embodiments of the invention the total area of the deflectable portions constitutes at least 20%, at least 30%, at least 40%, at least 50%, at least 60%, at least 70%, at least 80%, at least 90%, at least 95%, or more of the area of the wall that includes them. In certain preferred embodiments of the invention the total area of the deflectable portions constitutes at least 50% of the area of the wall that includes them, e.g., between 50% and 90%, between 60% and 80%, inclusive. In general, increasing the total area of the deflectable portions increases gas transfer. In certain embodiments of the invention the distance between adjacent deflectable portions is minimal, i.e., only as wide as the perimeter of the deflectable portions themselves.

The distance between adjacent deflectable portions need not be uniform, thus some adjacent portions may be separated by greater distances than others. The thickness of the deflectable portions, i.e., the distance between the interior of the chamber and the hollow cavity may vary depending, for example, on the diffusivity and/or permeability of the deflectable portion to $O_2$. Certain nonlimiting ranges for the thickness are: 1-1000 μm; 5-500 μm; 50-500 μm; and 100-300 μm, inclusive. Smaller and larger values for the thickness are also within the scope of the invention. The deflectable portions can assume a variety of cross-sectional shapes, and the cross-sectional shape can vary along the length of the deflectable portion. In certain embodiments of the invention the deflectable portion reaches the bottom of the chamber under conditions of maximum deflection. In certain embodiments of the invention deflection results in a complete seal, thereby dividing the chamber into multiple regions separated by the deflectable portions. However, it may be desirable to achieve less than a complete seal in order to allow fluid to flow backwards around the edges of the deflectable portion.

FIGS. 4A-4C show an enlarged view of the chamber and an actuation sequence of the deflectable portions to achieve peristaltic action. FIG. 4A shows a cross-sectional view of the chamber 12 (growth well) and hollow spaces 18 adjacent to deflectable portions 16 of the top wall in the unactuated state. FIG. 4B shows simultaneous actuation of the leftmost two deflectable portions, which may be achieved by pressuring the corresponding hollow spaces directly above. Deflection of the portions into the chamber causes displacement of the contents of the chamber below the deflected regions, forcing the contents to move elsewhere in the chamber. The increased pressure in the chamber results in upward displacement of the undeflected portions, as shown. FIG. 4C depicts subsequent de-actuation of the leftmost portion (e.g., by releasing the pressure in the hollow cavity above), continued deflection of the second portion, and actuation of the third portion from the left. Deflection of the third portion from the left pushes the chamber contents further in the rightward direction. In addition, upon release of the leftmost portion, chamber contents move backward into the region that was previously occupied by the deflected region.

The pattern shown in FIG. 4 proceeds to the right and wraps around to the left when it reaches the right edge. Thus according to this deflection sequence 2 portions are deflected at any given time. Such a sequence may be represented as follows, with a "0" representing an undeflected portion and a "1" representing a deflected portion: 0000000 (starting state); 1100000; 0110000; 0011000; 0001100; 0000110; 0000011; 1000001; 1100000 (return to first actuated state). FIG. 5 shows a top view of the deflection pattern in the unactuated state (FIG. 5A) and the first two actuated states. In FIG. 5B the two leftmost portions are deflected, and fluid is displaced to the right and upwards, i.e., the unactuated portions are displaced upwards into the overlying hollow cavities. In FIG. 5C the second portion remains deflected, the first portion is released, and the third portion is deflected. Fluid is pushed to the right by the third portion and around the second portion to push up the first portion.

Figure 6:
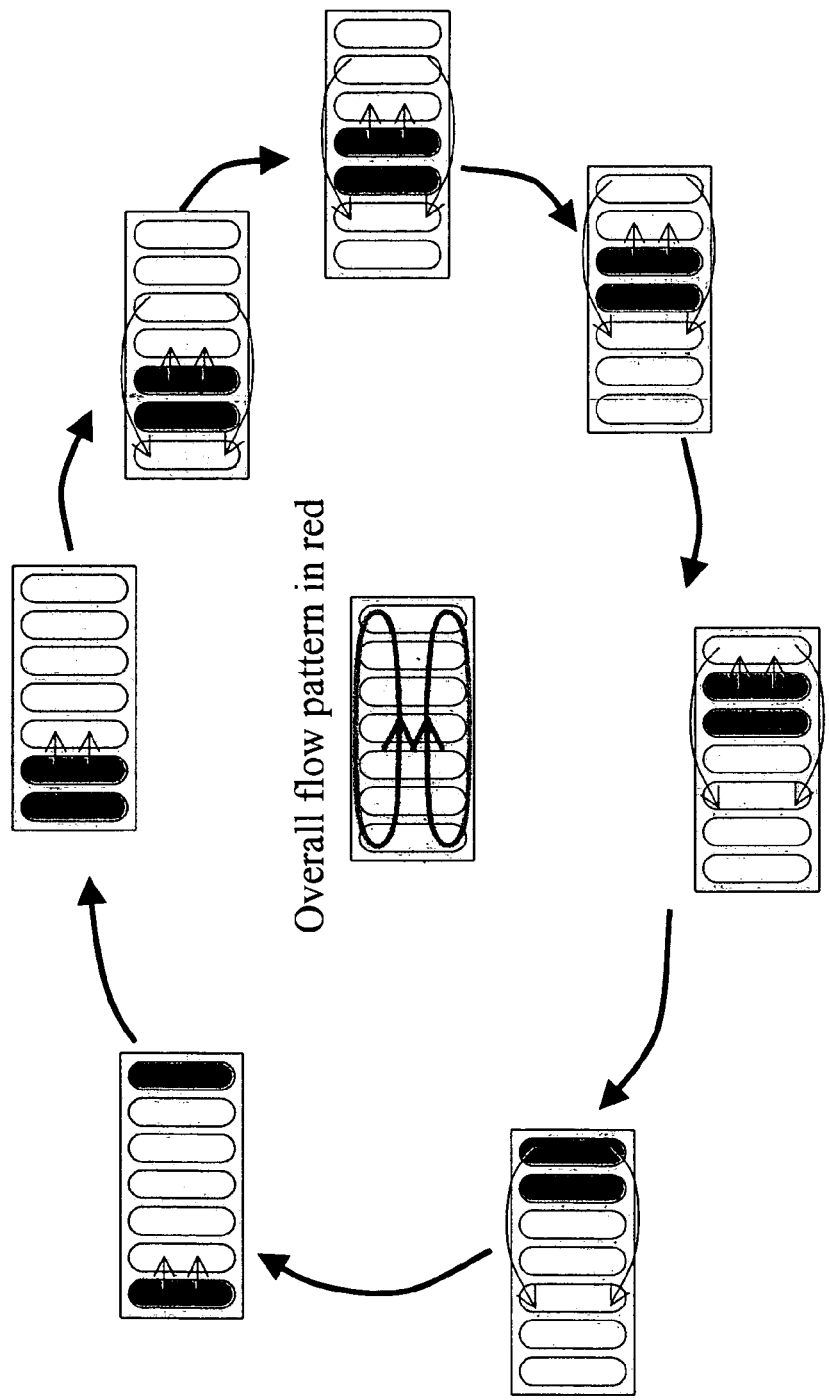
FIG. 6 shows the approximate flow of fluid in a chamber for deflectable portions with straight sides.

FIG. 6 shows the approximate flow of fluid in the chamber for straight deflectable portions deflected according to the sequence presented above. Large arrows indicate the actuation sequence. Small arrows in each chamber indicate the direction of fluid flow. The overall flow pattern is shown in the center of the figure. In general, the action of the device achieves an overall circular pattern of fluid flow rather than a unidirectional flow. Circulation of the fluid in this manner mixes the contents of the chamber. As the contents of the chamber move, they come into contact with the $O_2$-rich region near the deflectable portions, thereby increasing the rate of $O_2$ transfer. In general, a wide variety of different deflection sequences may be used. For example, a single portion may be deflected at any given time. Other suitable sequences include 1000001, 0100010, 0010100, 0001000, 0010100, 0100010, 1000001 (in which deflectable portions are sequentially pressurized beginning at either end of the wall and the deflection pattern goes back and forth in opposite directions); 1100000, 01100000, 0011000, 0001100, 0000110, 0000011, 0000110, 0001100, 0011000, 0110000, 1100000 (deflectable portions are deflected in groups of two but the pattern goes back and forth from opposite ends of the chamber instead of wrapping around), etc. It will be appreciated that the sequences will vary depending upon the number of deflectable portions.

In general, the deflection rate and the pressure that is applied to achieve deflection may vary. For example, certain nonlimiting ranges for the deflection rate (i.e., the rate at which the overall actuation state of the deflectable portions changes) are: 1-10,000 Hz; 5-5,000 Hz; 10-1,000 Hz; and 25-100 Hz, inclusive. Other exemplary and nonlimiting ranges are: 1-1000 Hz, 10-500 Hz, inclusive. Lower or higher values may also be used. Nonlimiting ranges for the pressure are: 1-200 psi; 1-100 psi; 1-30 psi; 5-30 psi; etc. In certain embodiments of the invention the rate at which pressurization (and therefore deflection) occurs is controllable, e.g., using a gas regulator or by introducing a restriction into the means that connects the hollow cavity with the gas reservoir.

In certain embodiments of the invention the selectively deflectable portions are independently deflectable, i.e., it is possible to deflect a single portion without deflecting any of the other portions. In other embodiments of the invention the portions are deflectable in groups or units of 2 or more, e.g., in groups of 2, 3, 4, 5, etc. The groups need not be adjacent. In embodiments of the invention in which the portions are selectively deflectable in groups, the portions in each group need not deflect at the same time. For example, the portions within a single group may deflect in a predetermined sequence, as described below, even where it is not possible to independently control the deflection of each portion.

Selective deflection of the portions may be achieved by connecting the hollow spaces to a high pressure reservoir via a valve. FIG. 7A shows a top view of embodiment in which each of 7 tube-shaped cavities 18 overlying deflectable portions of the top wall of a chamber is connected to an individual valve 20, e.g., a solenoid valve, via an actuation interface port. Each valve controls the flow of gas into the hollow cavity, thereby actuating or releasing the deflectable portion below. In this embodiment deflection of each portion is individually controllable, i.e., the portions can deflect independently of each other.

FIG. 7B shows an alternate design in which the 7 hollow cavities 18 comprise 3 groups (the first group comprises the leftmost two cavities, the second group comprises the three cavities in the middle, and the third group comprises the rightmost two cavities), each of which is controllable independent of the other 2 groups. One of the hollow cavities in each group (the leftmost cavity in each group) is connected to a valve 20, while the remaining cavities are not connected to a valve. A small hollow connection 22 exists between the members of each group. The leftmost cavity in each group is first to pressurize upon actuation of the valve to which it is connected. The cavity immediately to the right of each cavity connected to a valve pressurizes next, etc. The small size of the connection causes a delay so that the members of each group will pressurize in sequence rather than together.

In general, the deflectable portions may be equal in size and/or shape or they may have variable sizes and/or shapes. The portions depicted in FIG. 4 have straight sides that are substantially parallel to each other and thus have approximately uniform width. In addition, the portions extend across the surface of the chamber wall in a substantially parallel fashion with respect to one another. However, there is no requirement that the deflectable portions have this type of configuration, and the invention encompasses a wide variety of alternative designs. For example, in certain embodiments of the invention the width of the deflectable portions is less near the edges of the chamber than in the middle. Without wishing to be bound by any theory, introducing some asymmetry into the shape of the tubes is likely to result in improved mixing. For example, with the straight-sided deflectable portions, two flow circulations (upper and lower half as shown in FIG. 6) may stay separated and the top and bottom regions in the chamber may have different mixtures. By changing the widths of the deflectable portions, e.g., by introducing asymmetry, different types of flow patterns can be engineered. As mentioned above, the shape of the hollow cavity adjacent to each deflectable portion can, but need not, assume the same shape as the portion whose deflection it actuates.

FIG. 8 shows a schematic of a top view of an embodiment in which the width of the deflectable portions is variable and in which the portions do not all have identical shapes. Adjacent portions contain complementary convex and concave regions. Except for the middle portion, one side of each portion has both a concave and a convex region, which "fits" into complementary convex and concave regions on the adjacent portion. The other sides are straight. The middle portion contains two convex and two concave portions, which correspond to complementary concave and convex regions of the adjacent portions. Large arrows on FIG. 8 show the actuation sequence while small arrows on each chamber show the approximate direction of fluid flow. It will be appreciated that the direction of flow exhibits less uniformity than in the embodiment described above. The central image shows the overall direction of fluid flow. The action of the device results in a number of approximately circular flow patterns. Results (see below) indicate that mixing takes place considerably faster when cavities with variable widths are used.

In certain embodiments of the invention mixing of two initially unmixed liquids is substantially complete within 1 minute of actuation. In certain other embodiments of the invention mixing of two initially unmixed liquids is substantially complete within less than 1 minute of actuation, e.g., within 45 seconds, within 25 seconds, or within 10 seconds or less. In certain embodiments of the invention the device achieves an oxygen transfer rate of at least 0.05 mol/L/h, or preferably at least 0.1 mol/L/hr or at least 0.14 mol/L/hr. In certain embodiments of the invention the device achieves a $k_L a$ for $O_2$ of at least 0.05/sec, more preferably at least 0.1/sec, more preferably at least 0.2/sec. In certain embodiments of the invention the device supports growth of cells (e.g., bacteria) to achieve a cell density of at least $5 \times 10^9$ cells/ml, more preferably at least $10^{10}$ cells/ml, more preferably at least $2 \times 10^{10}$ cells/ml, yet more preferably at least $2.5 \times 10^{10}$ cells/ml.

As mentioned above, in certain preferred embodiments of the invention at least one of the hollow cavities is connected to an actuation interface port, e.g., a port via which pressurization/depressurization of the cavity can be accomplished. It is not necessary that each cavity is directly connected to such a port. For example, as described above, one or more of the cavities may instead be connected to a second cavity, so that pressurization of the first cavity results (e.g., after a delay) in pressurization of the second cavity. The actuation interface port is connected to a high pressure reservoir, e.g., via a valve. The actuation interface port also allows for venting, e.g., to a low pressure reservoir or to the atmosphere, for depressurization of the cavity. Any of a variety of standard methods can be used to connect the various fluidic components.

The high pressure reservoir can be, e.g., a gas tank such as a high pressure gas cylinder. One or more gas pressure regulators typically controls the pressure on a line that feeds into a manifold to which the actuation interface ports are connected. Alternately, in certain embodiments of the invention a smaller reservoir is used, in which a pressure sensor and a pump, which is activated when the pressure falls below a preselected value, can be used to control the pressure. As mentioned above, in certain embodiments of the invention the pressure reservoir is humidified, e.g., by including a vessel that contains water within the reservoir or by any other suitable means.

In certain embodiments of the invention one or more access ports, also referred to as injection ports, provides a means of adding material to and/or removing material from the interior of the chamber. For example, such an injection port can be used to introduce media and cells into a growth chamber prior to the beginning of a fermentation run. Additional substrates can be added during the run. Samples can also be taken during the course of the run, e.g., for determination of parameters such as pH, optical density (OD), dissolved oxygen, substrate or product concentration, etc. In certain embodiments of the invention between 1 and 10 injection ports, inclusive, interfaces with the injection chamber. The access ports can be capped when not in use to prevent evaporation of the contents of the chamber. In embodiments of the invention in which the access ports are fabricated from an elastomer, the ports are self-sealing. In other embodiments of the invention a septum that self-seals after puncturing may be used.

In general, the chamber is contained within a housing that serves to define the chamber. The hollow cavities may be contained within the same housing or within a separate housing that is in contact with the housing for the chamber. In certain embodiments of the invention the hollow cavities form an assembly of tube-shaped elements, which may be blind at one end or may be connected to other elements (e.g., valves, high pressure reservoir) at both ends.

III. Multichamber Devices

Figure 9A:
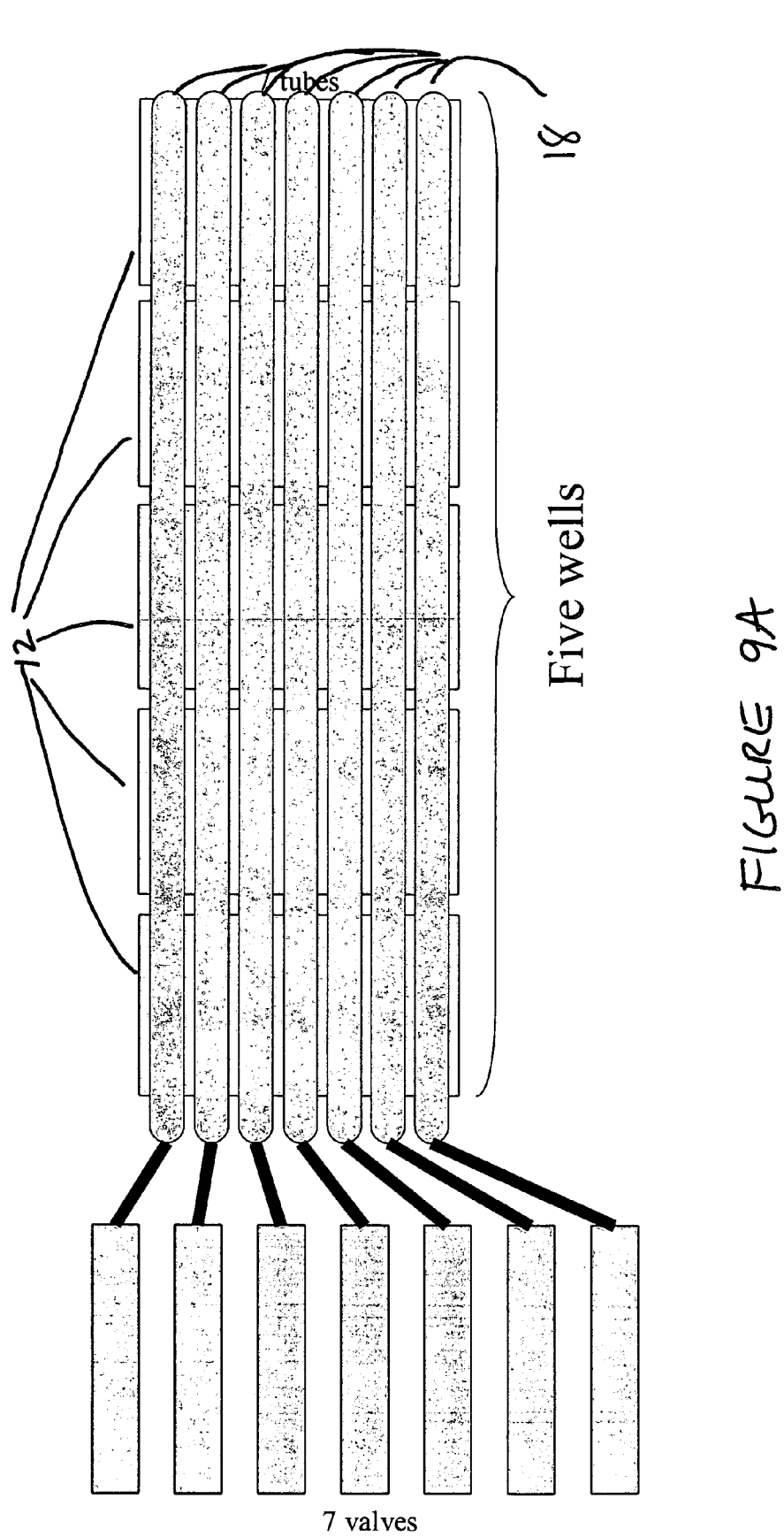
FIG. 9A shows an embodiment in which each of a plurality of hollow cavities (or tubes) extends over multiple chambers.

The discussion above focused on the features and operation of a device comprising a single chamber or well. However, an important aspect of the invention is that it is readily scalable to include multiple chambers. In particular, in certain embodiments of the invention the device contains multiple chambers without increasing the number of components such as actuation interface ports, actuators such as valves, etc. For example, FIG. 9A shows an embodiment in which each of a plurality of hollow cavities 18 (7 cavities) extends over multiple chambers 12 (5 chambers). Pressurization of a hollow cavity results in deflection of the deflectable portions of each chamber, where the chamber is in contact with the hollow cavity.

As is evident from FIG. 9A, each actuation interface port and associated actuator serves multiple chambers. Since the deflectable portions of each chamber deflect at the same rate and since the gas in the overlying hollow cavities has an essentially uniform $O_2$ concentration, conditions of mixing and oxygenation in the chambers will be virtually identical. Thus it is possible to carry out multiple fermentations in parallel, under essentially identical conditions of mixing and oxygenation. Multilayer structures in which a second layer of chambers overlies the cavities are also encompassed by the invention to achieve even greater scalability. For example according to this embodiment each cavity in FIG. 9A would actuate 10 chambers, 5 below and 5 above the cavities.

Figure 9B:
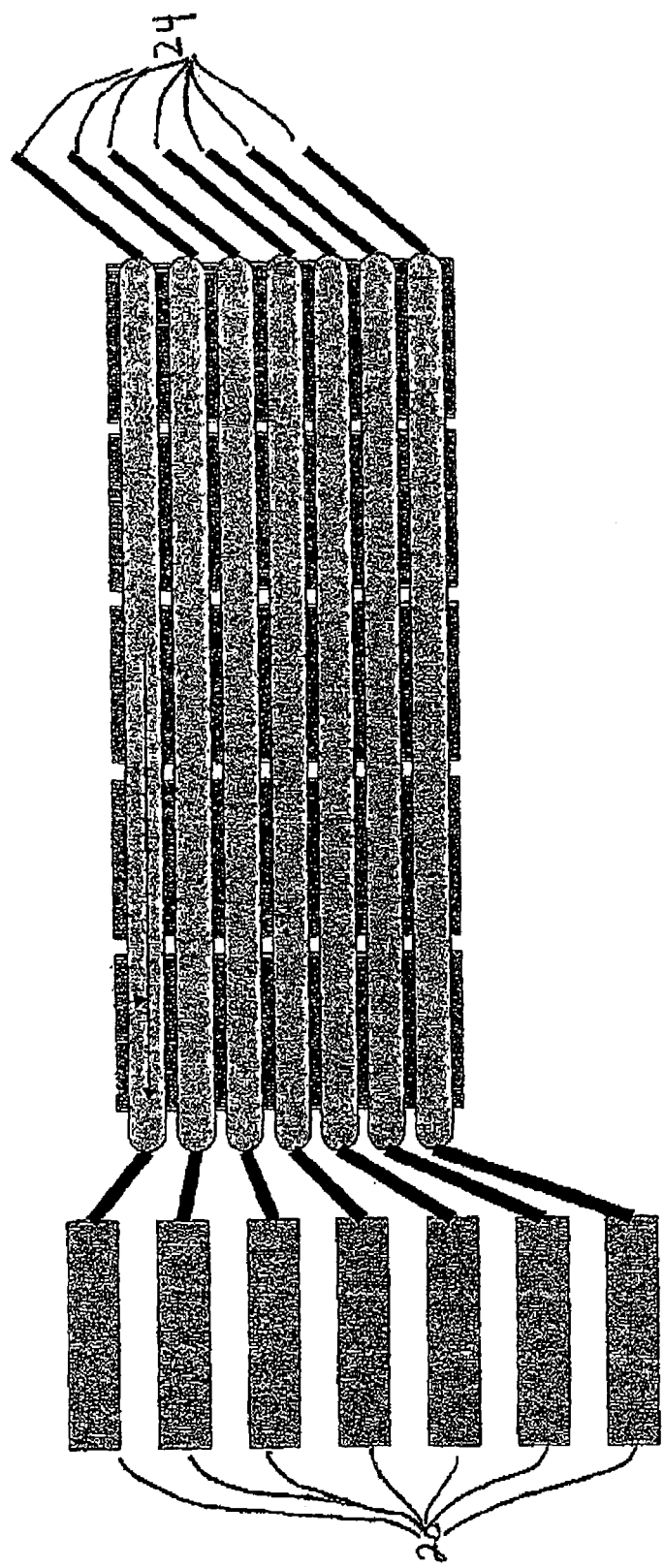
FIG. 9B shows an embodiment in which the hollow cavities (or tubes) are connected to a high pressure line at one end and a valve at the other end, such that the cavity is pressurized when the valve is closed and depressurized when the valve is open to allow gas flow.

In the embodiment shown in FIG. 9A, each cavity is blind at one end and connected to a high pressure reservoir at the other end (via an actuator). FIG. 9B shows an alternative embodiment in which the cavities (or tubes) are connected at one end to a high pressure reservoir via a line 24 and at the other end to a valve 20 which can be vented to the atmosphere or to a low pressure reservoir. When a valve is closed, the corresponding cavity is pressurized, resulting in deflection. When the valve is opened, gas flows through the cavity and the cavity is depressurized. This may aid in maintaining a fresh supply of gas to the cavity. In the embodiment shown in FIG. 9B, the cavities are not interconnected. In other embodiments the cavities are interconnected via connecting portions that have a small cross-sectional area compared with the cross-sectional area of the cavities (e.g., as described above), and fewer valves are used than the number of cavities. FIG. 9B depicts a multichamber device, however the same principle may be applied to construct single-chamber devices.

IV. Materials

In general, a wide variety of materials may be used to construct the various elements of the devices of the invention. In certain embodiments of the invention the deflectable portions of the wall(s) are made of a flexible, oxygen-permeable material such as polydimethylsiloxane (PDMS), or a material having similar values, for oxygen diffusivity (D) and/or solubility (S). For example, for PDMS, $D=3.4 \times 10^{-5}$ cm$^2$/s and $S=1.5\times10^{-3}$ mol/Liter (for air at 1 atm). In general, materials having a diffusivity for $O_2$ greater than $0.5\times10^{-5}$ cm$^2$/s and/or S for $O_2$ greater than $0.15\times10^{-3}$ mol/Liter (for air at 1 atm) may be used. In certain embodiments of the invention a material having a diffusivity for $O_2$ greater than $1.0\times10^{-5}$ cm$^2$/s, greater than $2.0\times10^{-5}$ cm$^2$/s, or greater than $3.0\times10^{-5}$ cm$^2$/s is used. In certain embodiments of the invention a material having a solubility for $O_2$ greater than $0.3\times10^{-3}$ mol/Liter, greater than $0.5\times10^{-3}$ mol/Liter, or greater than $1.0\times10^{-3}$ mol/Liter (all for air at 1 atm) is used. Preferred values for $O_2$ permeability (P) may be calculated using the relationship $D \times S = P$. For example, in certain embodiments of the invention the permeability of the membrane to oxygen is approximately equal to that of PDMS, i.e., 800 Barrer (1 Barrer=10-10 cm$^3$(STP) cm/cm$^2$ s cm Hg) (T. C. Merkel, et al., "Gas sorption, diffusion, and permeation in poly(dimethylsiloxane)", *J. of Polymer Science, Part B-Polymer Physics*, vol. 38, pp 1415-434, 2000) (e.g., between 750-850 Barrer). In certain other embodiments of the invention the permeability of the membrane to oxygen is greater than 800 Barrer, e.g., between 800-1000 Barrer. In certain other embodiments of the invention the permeability of the membrane to oxygen is either between approximately 600 and 800 Barrer, between approximately 400 and 600 Barrer, between approximately 200 and 400 Barrer, or between approximately 40 and 200 Barrer (all ranges inclusive). Preferably the material is also permeable to $CO_2$ and is substantially impermeable to liquids. It will be appreciated that suitable values for D and S will depend on a variety of parameters including, for example, the concentration of $O_2$ in the gas or fluid that is used to pressurize the hollow cavities, the actuation rate, and the desired level of $O_2$ in the chamber, which may vary, for example, depending on the type of cells to be cultured therein. Standard methods for measuring $O_2$ permeability may be used if desired, e.g., as defined by the American Society of Testing and Materials D3985 standard (ASTM, 1995).

In certain embodiments of the invention the deflectable portions are made of an elastomeric material, by which is meant a polymer that exists at a temperature between its glass transition temperature and its liquefaction temperature (Allcock, F., et al., *Contemporary Polymer Chemistry*, 3rd Ed., Prentice Hall, 2003). In general, such materials deform when force is applied and then return to their original shape when the force is removed. Thus fabrication of the deflectable portions from an elastomeric material allows them to stretch as they deflect in response to pressurization of an adjacent hollow space and then return to their prior shape upon depressurization and/or in response to increased pressure in the chamber resulting from deflection of another portion of the wall and subsequent backwards fluid flow. U.S. Pat. No. 6,408,878 lists a wide variety of elastomeric materials that can be used for fabrication of the deflectable portions, taking into account the needs for sufficient gas permeability and strength.

In certain embodiments of the invention an elastomeric material is used to fabricate various components of the device in addition to the deflectable portions. For example, the wall that contains the deflectable portions can be made entirely of an elastomeric material, e.g., an elastomeric membrane, which is positioned between the interior of the chamber and the interior of the hollow spaces. The hollow spaces may be fabricated as cavities within an elastomeric structure as may the chambers themselves. In these embodiments of the invention the housing therefore comprises one or more elastomeric blocks that contain the chambers and hollow cavities. Additional advantages of an elastomeric material include the fact that it is self-sealing and that it forms a strong yet reversible bond to a variety of materials such as glass. Yet another advantage is its transparency, which allows the use of optical sensing (e.g., using spectrometer(s)) for monitoring the contents of the chamber, e.g., for monitoring pH, dissolved oxygen, and optical density. An elastomeric device of the invention may conveniently be fabricated as described below. Preferably the material that forms the inner surface of the chamber walls is biocompatible. In certain embodiments of the invention the inner surfaces of the chamber walls are treated, e.g., with a substance that reduces the adherence of cells and/or potential synthetic products such as proteins.

Alternately, the housing may be fabricated from any of a variety of solid materials such as glass, plastics (e.g., thermoplastics such as polycarbonate or polymethylmethacrylate), silicon, or another metal such as stainless steel, aluminum, etc. Other suitable materials include photoresists such as SU-8. Appropriate recesses to form the chamber(s) and hollow spaces are enclosed within the housing. Separate units may contain the chamber and the hollow spaces, and a gas-permeable membrane to form the wall of the chamber that contains the deflectable portions is attached between the two units, e.g, using a suitable adhesive or bonding substance, heat fusion, etc.

V. Methods of Manufacture

Appropriate manufacturing techniques will vary depending on the materials from which the device is fabricated. For example, machining (e.g, conventional machining, micromachining, etc.) is suitable for materials such as glass and silicon or other metals, e.g., stainless steel, aluminum, etc., plastics, e.g., polycarbonate, polymethylmethacrylate, nylons, etc. Injection molding is useful for materials such as thermoplastics and rubbers. Hot embossing, laser ablation, and in situ construction (e.g., by building up layers of a material such as a photoresist) can also be used. Photolithography and etching can also be used for glass (e.g., Foturan™ glass) A number of these techniques have been employed in the fabrication of microscale devices (Heckele, M., et al., *Microsyst. Technol.*, 4:122-24, 1998; Martynova, L., et al., *Anal. Chem.*, 69:4783-89, 1997; Beebe, D., et al., *Proc. Natl. Acad. Sci.* 97:13488-93, 2000; Roberts, M., et al., *Anal. Chem.*, 69:203542, 1997; Pethig, R., et al., *J. Micromech. Microeng.*, 8:57-63, 1998; Tjerkstr, R., et al., *Electrochim. Acta* 42:3399-406, 1997; Bohm, S., et al., *Sens. Actuators A*, 77:223-28, 1999; Gad-el-Hak M., ed. *The MEMS Handbook*. New York: CRC, 2002).

In certain preferred embodiments of the invention soft lithography is used to fabricate the device. In general, as used herein, soft lithography refers to the molding of a two-part polymer (elastomer and curing agent), typically polydimethylsiloxane (PDMS), using masters. For example, to create a chamber, a mold with a raised projection is formed. The liquid polymer is cast or poured onto the mold and cured. The resulting structure is then removed from the mold, leaving a hollow area that was previously occupied by the raised projection. Standard techniques (e.g., techniques used in the semiconductor manufacturing industry) such as micromachining or photolithography (Madou, M., *Fundamentals of Microfabrication*. Boca Raton, Fla.: CRC, 1997; Quirk, M., and Serda, J., *Semiconductor Manufacturing Technology*, Prentice Hall, 2000) can be used to create masters to mold PDMS structures. Masks with which to create the masters using photolithography can conveniently be made using high resolution transparency films (Duffy, D. C., et al., *Anal. Chem.*, 70:4974-4984, 1998).

In certain embodiments of the invention a variation of the soft lithography technique known as multilayer soft lithography is used to fabricate the devices. Multilayer soft lithography and suitable materials are extensively described in U.S. Pat. No. 6,408,878, and in T. Thorsen, S. J. Maerkl, and S. R. Quake, "Microfluidic Large Scale Integration," Science, vol. 298, pp. 580-584, 2002 and M. A. Unger, H.-P. Chou, T. Thorsen, A. Scherer, and S. R. Quake, "Monolithic Microfabricated Valves and Pumps by Multilayer Soft Lithography," Science, vol. 288, pp. 113-116, 2000. (See also U.S. Patent Application Nos. 20020144738, 20020037499, 20020058332, 20030019833, 20010054778, 200100337956 and Anderson, J. R., et al., "Fabrication of Topologically Complex Three-Dimesional Microfluidic Systems in PDMS by Rapid Prototyping", *Anal. Chem.*, 72: 3158-3164, 2000.) As described therein, multilayer elastomeric structures can be fabricated in a number of different ways. Briefly, according to a preferred approach individual device layers are formed using different ratios of polymer to curing agent. In general, one layer has excess polymer relative to curing agent and a second layer has excess curing agent relative to polymer. The layers are partially cured and are then apposed to one another. The resulting structure is then subjected to an additional curing step. During this step diffusion between the layers occurs, so that after curing the layers form a single unitary structure. Multilayer structures can be constructed using a plurality of layers with alternating bias. Polymers such as Sylgard 182, 184, or 186 (Dow Chemical) are suitable as are a wide variety of different silicones and other materials. Alternatively, multilayer structures can be fabricated using a sacrificial layer technique. According to this approach a layer of elastomer is deposited on a substrate, and a sacrificial material such as a photoresist is then deposited to form what will ultimately become hollow regions such as chambers and cavities. A second layer of elastomer is deposited, encapsulating the sacrificial layer. After curing, the sacrificial layer is removed, leaving hollow regions within the multilayer structure. Other methods for fabricating layered structures can also be used.

The devices of the invention can be fabricated in a number of different ways using the multilayer soft lithography technique. For example, a 2-layer device can be constructed in which the chamber(s) are defined in a single layer, e.g., by pouring the elastomer over a mold with a raised projection. Preferably the polymer is spun after pouring so that only a thin layer remains on the top of the raised projection. This thin layer or membrane forms the upper surface of the resulting structure and serves as the top of the chamber. The bottom may be formed by positioning the structure on a rigid substrate such as glass, plastic, or metal. The hollow cavities are similarly defined in a second layer of elastomer which may be the same or different, provided that diffusion can occur between the two layers as described above. (Alternately, a traditional soft lithography method can be used and the two layers can be bonded, e.g., using an adhesive such as an epoxy or alternate bonding method.) The two layers are positioned so that the cavities overlie the chamber(s). After alignment the structure is subjected to curing. Pressurization of a hollow cavity results in deflection of the portion of the top of the chamber below the cavity.

FIG. 10 presents an overview of a multilayer soft lithography fabrication process that was used to implement a device of the invention as described in further detail below. FIG. 10A shows the process of making a mold on a silicon wafer using photolithography with masks created from high resolution transparencies. The mask on the left is used to form the mold for the chambers and injection ports. The mask on the right is used to form the mold for the cavities and shows a variety of different cavity configurations. FIG. 10B shows casting and partial curing of the two elastomeric layers defining the chambers (below) and the cavities (above). FIG. 10C shows the step of peeling the layer that defines the cavities from the wafer and punching holes to facilitate access to the cavities (referred to as tubes on the figure). FIG. 10D shows alignment of the layer defining the cavities with the layer defining the chambers, followed by full cure. FIG. 10E shows removing the individual devices from the mold. FIG. 10F shows the final step of sealing the device to a substrate (in this case a microscope slide) and includes the optional step of additional baking, which has been found to improve adherence of the device to the slide and also is of use when devices are reused (to bake off any remaining liquid prior to reuse). In this embodiment of the invenention the elastomeric housing defines the chamber and the substrate provides the lower wall of the chamber.

FIG. 11 shows an alternative embodiment of the invention in which two devices are sealed back to back to form a device in which two walls comprise selectably deflectable portions.

Alternately, a 3-layer device can be fabricated. The chambers are formed in a similar manner as above, except that a thicker layer of polymer is used on top of the raised projection. The structure is peeled from the mold and inverted, so that the layer of polymer forms the bottom of the chamber. The hollow cavities are similarly defined. A separate layer or membrane is also produced and is positioned between the chamber and the layer that forms the hollow cavities. This membrane forms the top of the chamber. The layer containing the hollow cavities is aligned so that the cavities overlie the chamber(s) and the resulting 3-layer structure is cured. Alternately, the layers can be bonded using an adhesive or other bonding method.

It will be evident that a number of variations on the above may be used. It is possible to construct devices having more than 3 layers. For example, according to certain embodiments of the invention a multilayer structure including a plurality of layers comprising chambers is constructed, in which the layers are positioned on top of one another and are separated by layers containing cavities. In certain embodiments of this approach pressurization of a cavity causes deflection into both a chamber positioned above the cavity and a chamber positioned below the cavity.

Various materials and manufacturing techniques can be combined. FIG. 12 shows an embodiment of the invention in which a layer defining cavities is fabricated either using an elastomer or from a material such as glass, plastic, or metal. A layer defining chambers is fabricated from glass, metal, or plastic using any of the appropriate manufacturing methods mentioned above. A gas-permeable membrane is fabricated (e.g., from an elastomeric material such as PDMS) and is positioned between the layers defining the cavities and chambers, which are aligned appropriately. The 3-layer device is then sealed.

VI. Construction and Testing of an Exemplary Device

Figure 13:
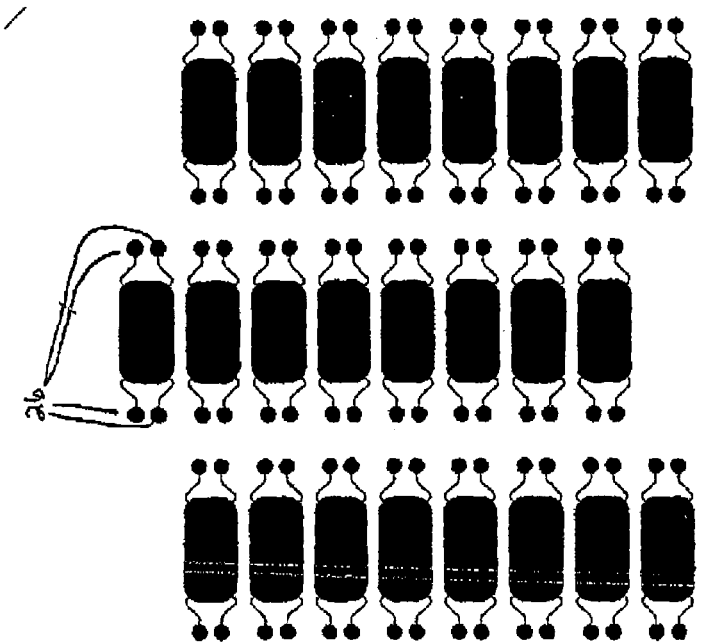
FIG. 13 shows an example of a mask for a chamber mold in enlarged format.

A multichamber device of the invention was fabricated using a multilayer soft lithography technique. Masks were created using transparencies. FIG. 13 shows the mask for the chamber mold in enlarged format. In the actual mask, the dashed circle would be 3.5 inches in diameter and each chamber is 5 mm×10 mm. Each chamber interfaces with 4 injection ports 26. The mask was used to create a mold on a silicon wafer substrate using the photoresist SU-8 according to standard semiconductor manufacturing methods. Dark areas on the mask result in raised structures, typically 300-500 µm, on the mold, which corresponds to the depth of the resulting chamber. A two part silicone elastomer polymer (Sylgard 184 elastomer from Dow Chemical) was mixed at a 20:1 ratio of polymer to curing agent (normal mixing ratio for this elastomer is 10:1), poured over the mold, and spun to leave a layer a few hundred microns in thickness, resulting in a membrane of material which forms the top of the chamber, portions of which deflect into the chamber. The structure was cured at 65° C. for 20 minutes. The dark areas shown in FIG. 13 correspond to cavities in the elastomer structure.

Figure 14:
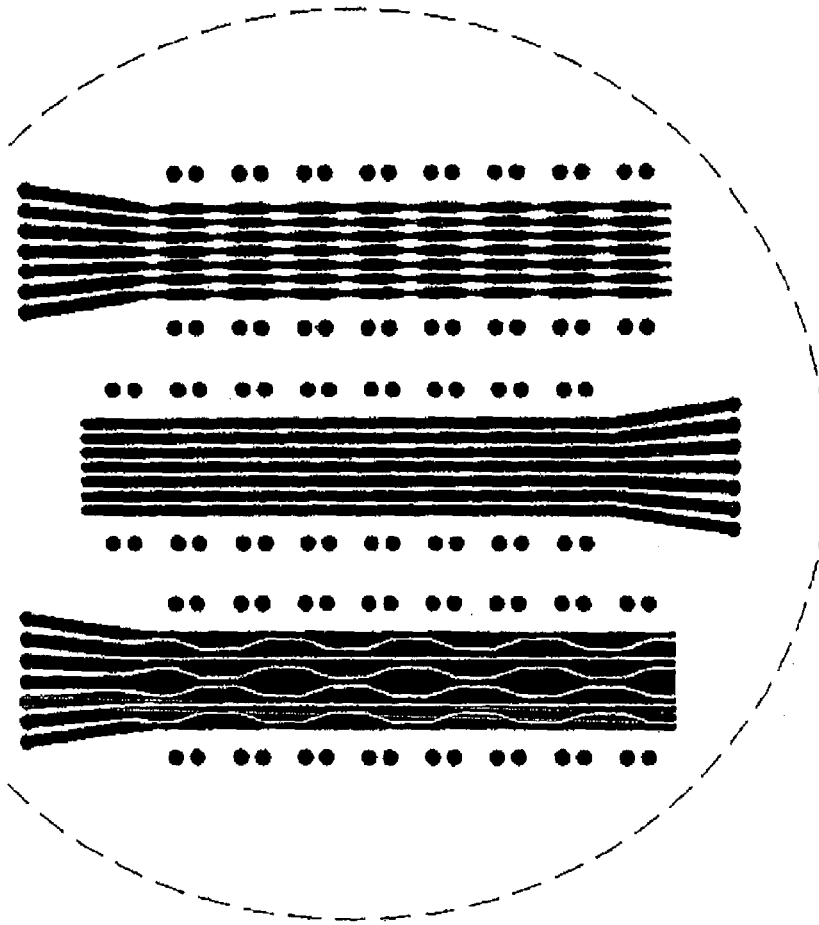
FIG. 14 shows an example of a mask for several different cavity molds in which the cavities (and thus the deflectable portions) have either straight sides (middle), sides of non-uniform width containing complementary concave and convex portions (left), or sides that are narrower near the edge of the underlying chamber than near the middle (right).

FIG. 14 shows a mask for three different assemblies of hollow spaces. The leftmost mask is used to create hollow spaces or voids with corresponding convex and concave portions as described above. The middle mask is used to create cavities with straight sides. The rightmost mask is used to create cavities with narrower regions near the edges of the underlying chambers. The dark areas on the mask result in raised structures of SU-8 (typically 200-400 µm) on a silicon wafer substrate to form the mold. The dark areas shown on FIG. 14 correspond to cavities in the elastomer structure and to deflectable portions of the wall of the chamber that ultimately underlies the cavities. The elastomer was mixed at an 8:1 ratio of polymer to curing agent and poured over the mold in a layer approximately 3-4 mm thick. The structure was cured at 65° C. for 50 minutes and was then peeled from the mold. It will be appreciated that the resulting structure comprises an assembly of tube-shaped structures with blind ends. The wider portion at each end of the tubes corresponds to an actuation interface port. The 4 small circles adjacent to each chamber mold form part of the injection ports and facilitate alignment of the two layers of the structure.

Following removal of the chamber and hollow cavity (tube) assemblies from their molds, holes are punched in the latter to facilitate entry of a needle that serves as the actuation interface. The tube assembly is aligned with the partially cured chamber structures (still attached to the chamber mold) and the resulting 2-layer structure was cured for 2 hours at 65° C. Individual devices were then cut from the chamber mold and sealed to glass microscope slides. The devices were then cured at 65° C. for at least an additional 2 hours.

Figure 15:
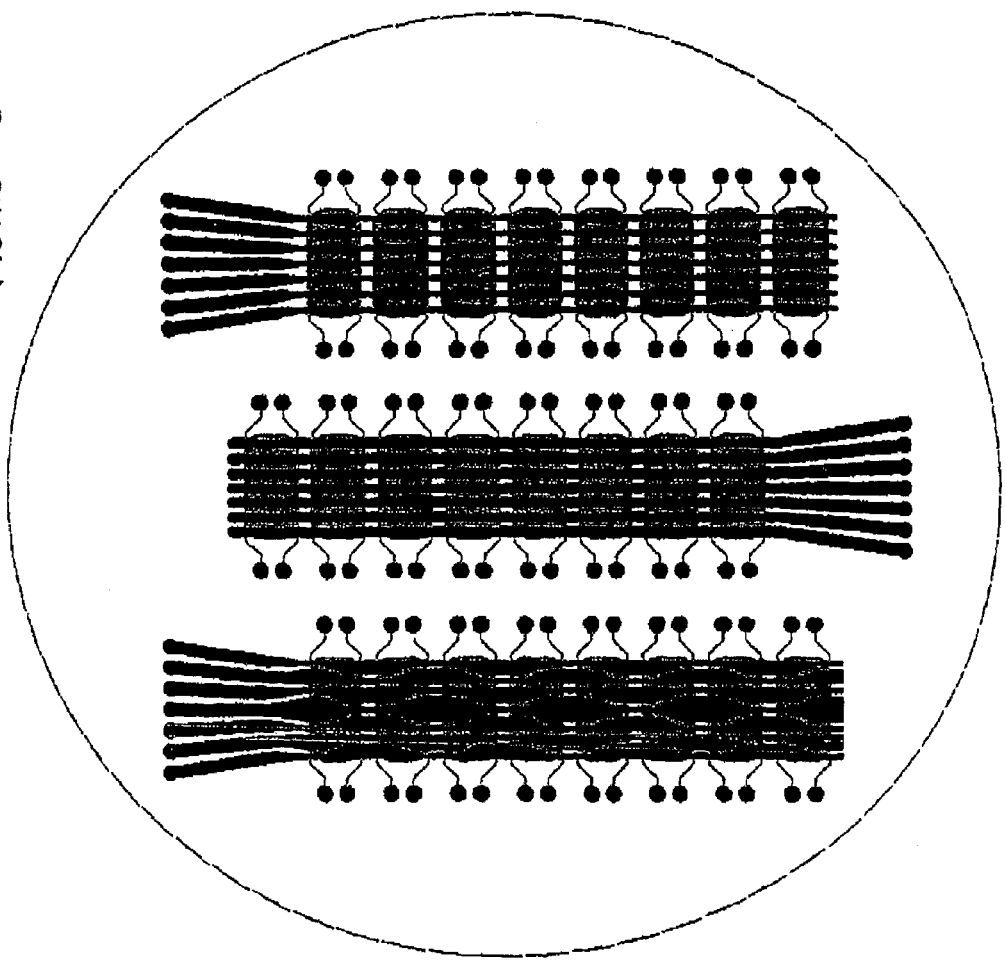
FIG. 15 shows the two masks of FIGS. 13 and 14 overlaid and provides a top view of the overall structure of the device prior to interfacing with the high pressure reservoir.

FIG. 15 shows the two masks of FIGS. 13 and 14 overlaid and provides a top view of the overall structure of the device prior to interfacing with the high pressure reservoir, etc. The scalability of the device may readily be appreciated. As shown, 7 tube assemblies extend over 8 chambers. Thus 7 valves actuate 8 chambers. By increasing the length of the tube assemblies additional chambers (e.g., 16, 32, 64 or even more) could be accommodated. Minimizing the number of actuators reduces overall system size and simplifies the assembly of the macroscopic actuators.

Figure 16:
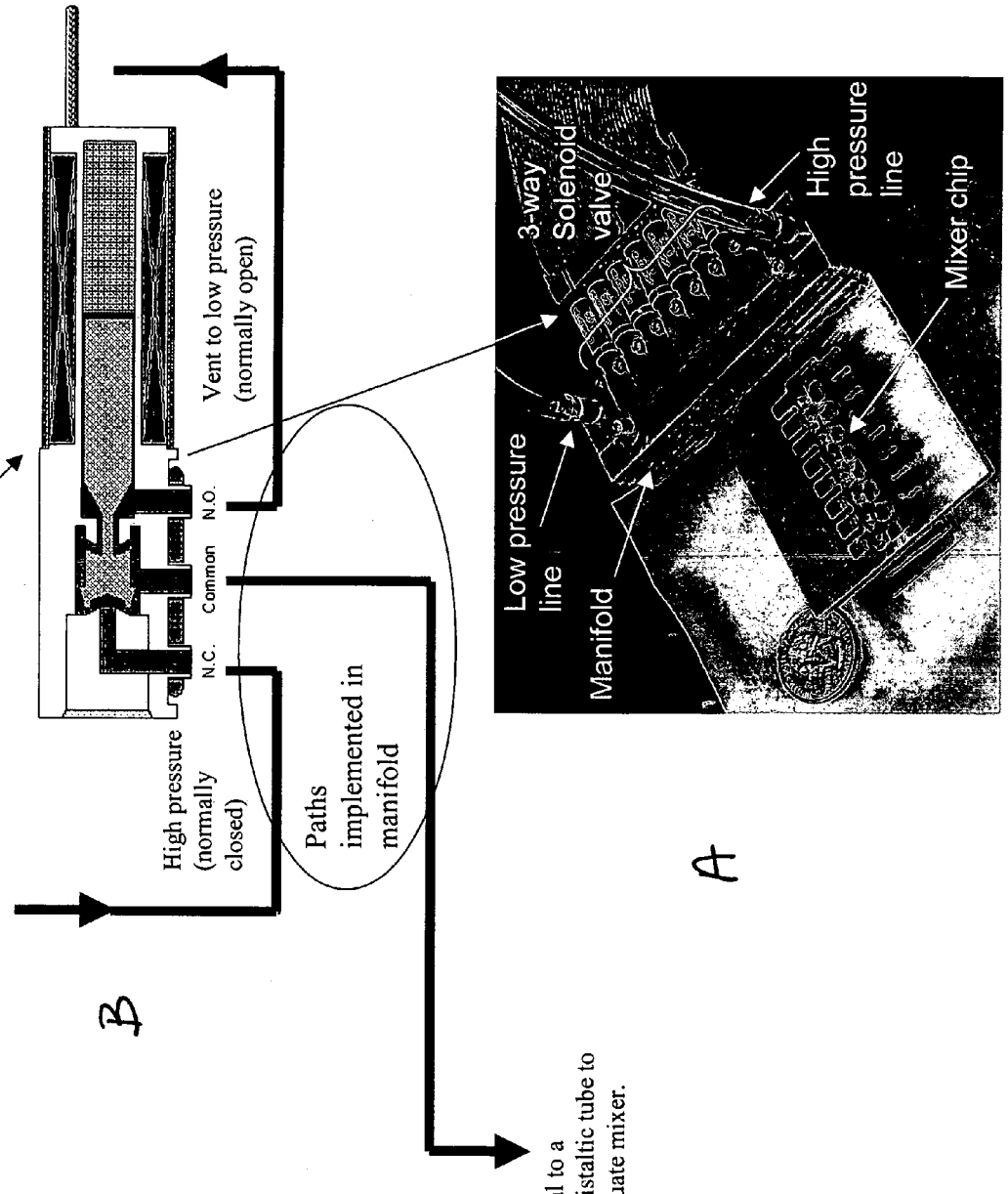
FIG. 16A shows a device made using multilayer soft lithography as described above (with straight-sided cavities) interfaced with a high pressure reservoir.
FIG. 16B presents a schematic diagram of the valve and the paths that are implemented in the manifold.
Figure 17:
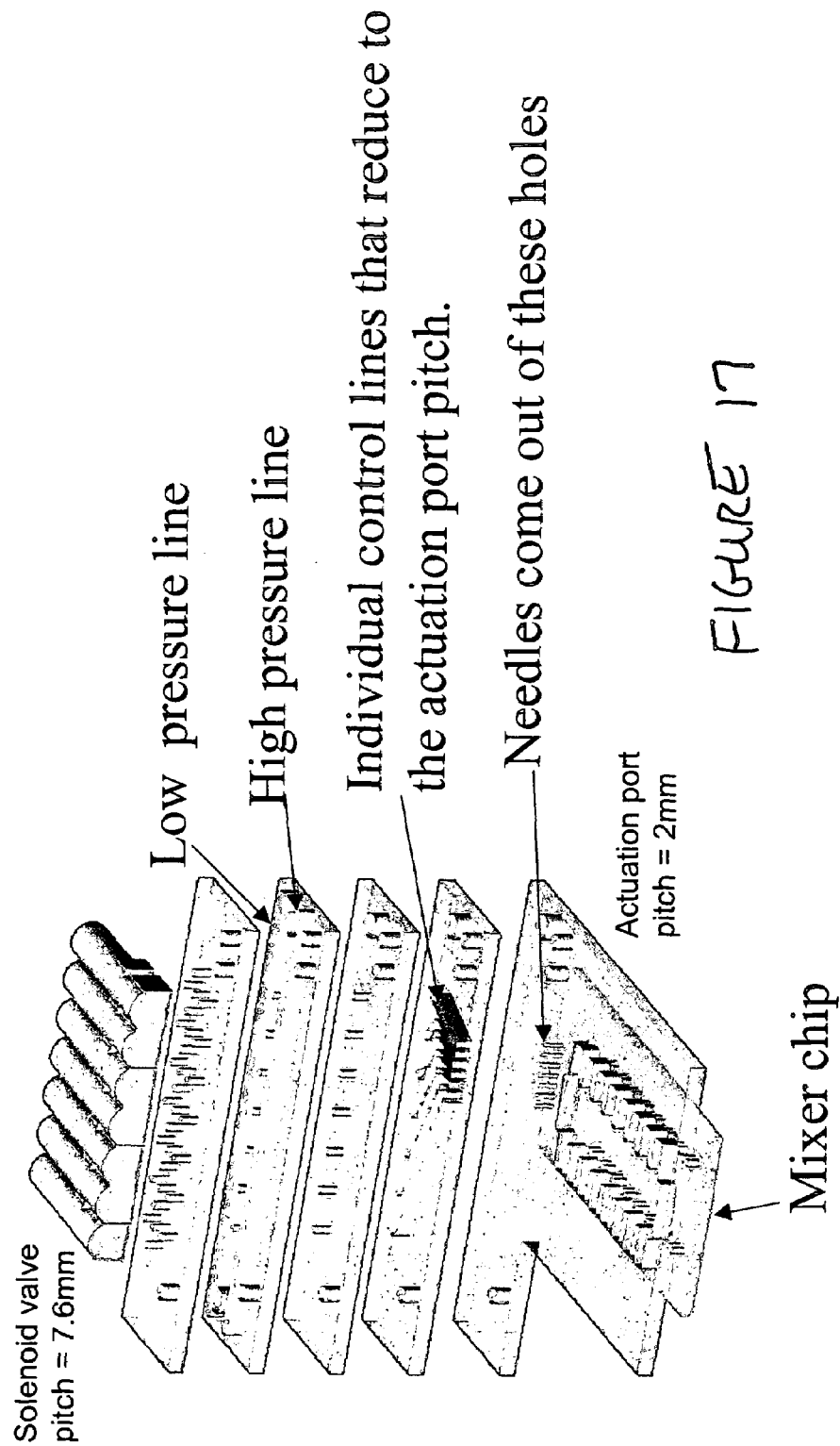
FIG. 17 shows an exploded view of the manifold and the paths implemented therein.

FIG. 16A shows a device made as described above (with straight tubes) interfaced with a high pressure reservoir. Needles extend from the actuation interface ports at the end of each cavity into the manifold, in which they are connected to high density 3-way solenoid valves (LHDA0523112H, Lee Company). Alternate valve systems could also be used. Pressurization of the cavities is controlled by a computer. TTL logic signals indicate when a cavity should be pressurized and energize the solenoid valve that connects the cavity to the high pressure reservoir (a gas cylinder containing air). A special purpose digital circuit could also be used. FIG. 16B presents a schematic diagram of the valve and the paths that are implemented in the manifold. FIG. 17 shows an exploded view of the manifold and the paths implemented therein.

FIG. 18 shows a larger view of the device in which the actuation interface ports and injection ports are visible. Two distinct dyes in water were injected into at opposite ends of the device via the injection ports. The device was actuated at 100 Hz, ~10 psi. FIG. 19 presents a sequence of images showing the progress of mixing. The upper left image shows mixing in an unactuated device at t>1 hour after injection of the dyed water into the chamber. It is evident that very little mixing has occurred. The image in the upper right shows the chamber 5 seconds after actuation. The lower images show mixing after 20 seconds (left) and 45 seconds (right) of actuation. By 45 seconds the contents of the chamber are almost a uniform mixture of the two dyes.

FIG. 20 shows a similar sequence for the mixing of Columbo™ yogurt and dye in water (viscosity 1 cp). Dual circulation flow is evident, and mixing takes place in approximately 18 minutes, demonstrating the ability of the device to mix even extremely viscous fluids. Mixing of diluted corn syrup (estimated viscosity of 1500 cp) has also been demonstrated (not shown).

Figure 21:
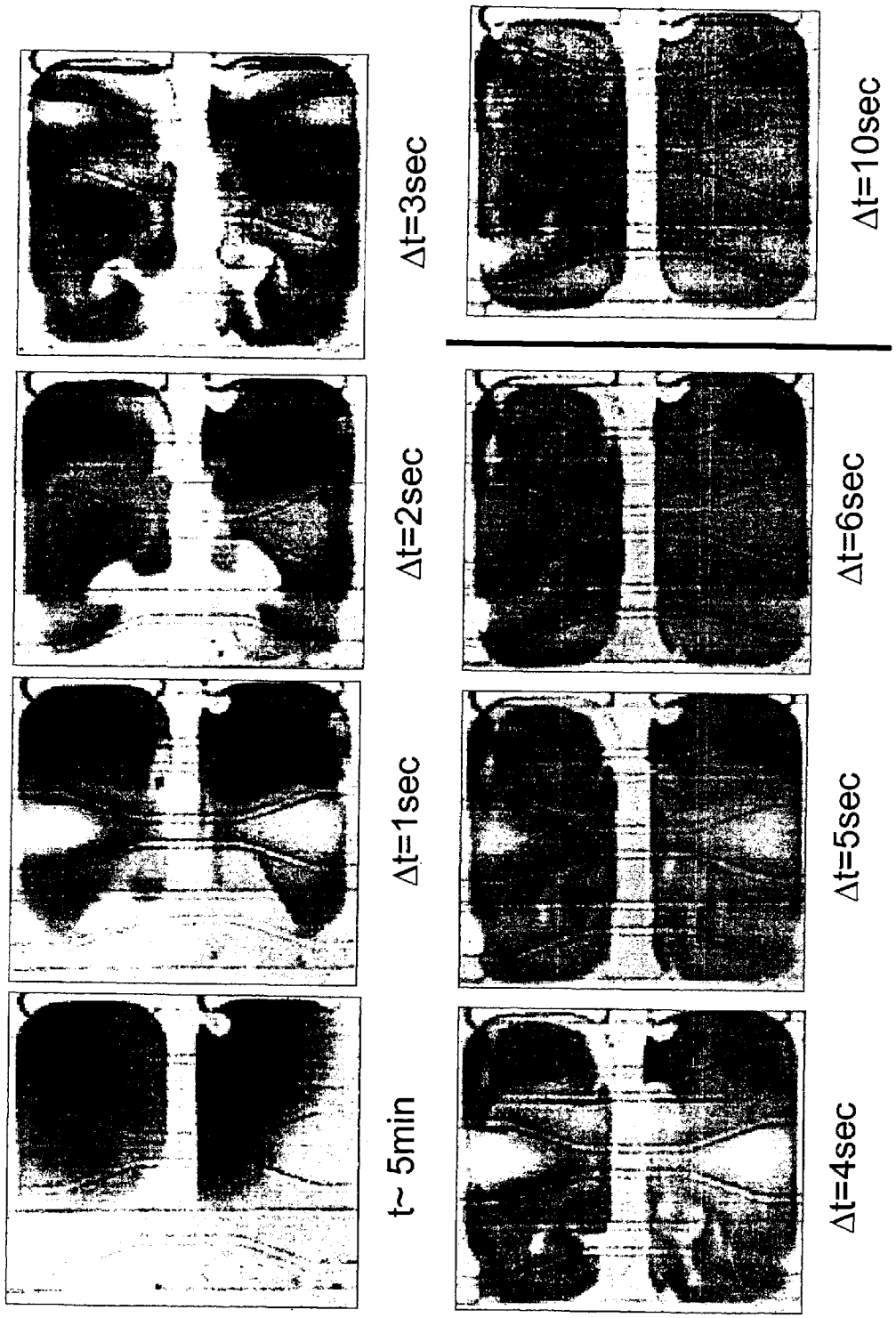
FIG. 21 shows mixing achieved using a device comprising deflectable portions and cavities (tubes) with nonuniform widths.

FIG. 21 shows mixing achieved by a device similar to that described above except using cavities (tubes) with nonuniform widths (as shown in the middle mask in FIG. 14. Dye in water containing 600 g/L glucose (1<viscosity<50 cp) was injected into an access port at one end of the chamber. The deflection rate was 100 Hz, and the pressure was 8 psi. Local circulation flows can be seen. As is evident, mixing is achieved considerably more rapidly using tubes with non-uniform widths than with the straight-sided tubes.

Figure 22:
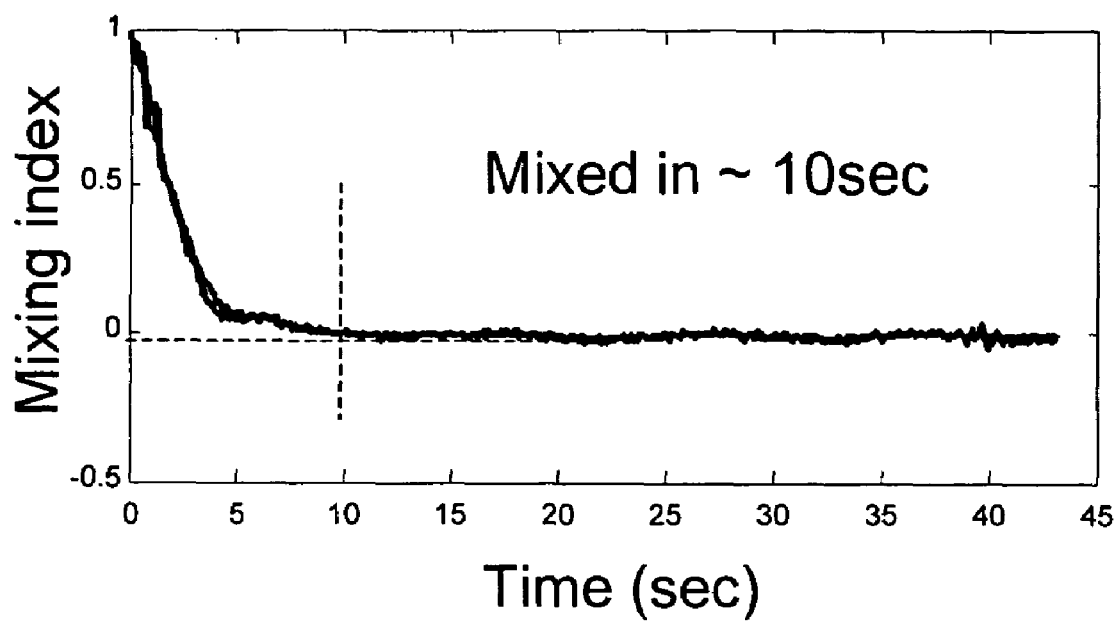
FIG. 22 is a plot showing the mixing time (mixing index) for a device comprising deflectable portions and cavities (tubes) with nonuniform widths. Mixing is complete in approximately 10 seconds.

FIG. 22 is a plot showing the mixing time (mixing index) using a device in which the deflectable portions and cavities have nonuniform widths (as shown in the middle mask in FIG. 14). The mixing index was computed by obtaining a matrix of Red, Green, and Blue at intervals over a time course of approximately 45 seconds using a color CCD video camera. To obtain the "blue level" the mean of RGB for each pixel was subtracted from the Blue matrix. The data was normalized so that a value of 1 for the mixing index corresponds to the unmixed (t=0) state and a value of 0 corresponds to the fully mixed (t=10) state. The expression for the mixing index is given by: $1/N \cdot (\Sigma_i |b_i - b_{av}|)/b_{av}$ where b represents number of pixels in Blue matrix, $b_{av}$ represents average number of pixels in RGB matrix, and N represents the total number of pixels. Mixing is complete in approximately 10 seconds.

Figure 23:
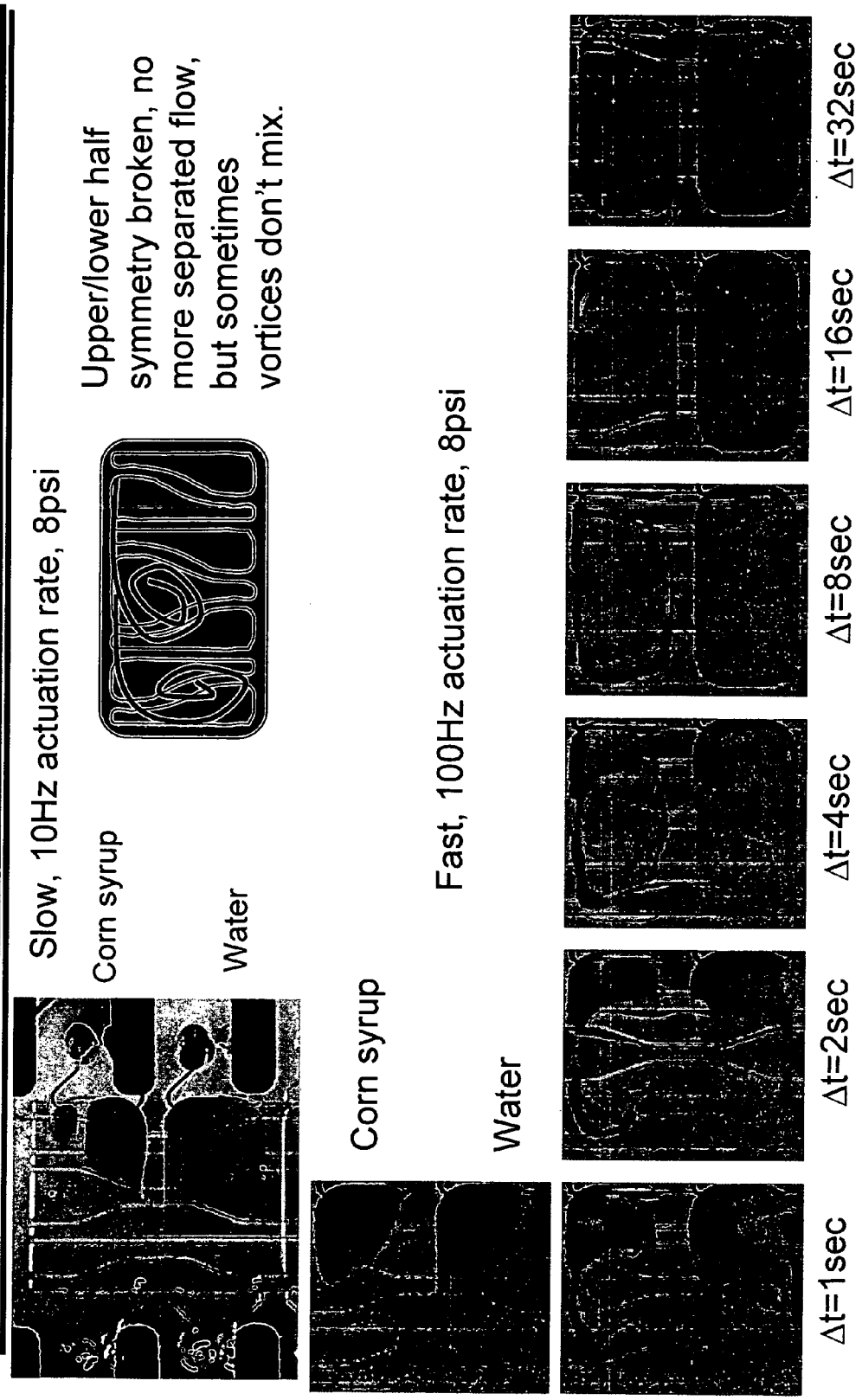
FIG. 23 shows images and a schematic diagram of mixing achieved using a device with cavities (tubes) with nonuniform widths as shown in the middle mask in FIG. 14.

FIG. 23 is another sequence showing mixing achieved by a device with cavities (tubes) with nonuniform widths as shown in the middle mask in FIG. 14. Dye in water or in water containing light corn syrup (1500 cp) was injected into an access port at one end of the chamber. As indicated, the upper left image shows deflection at 10 Hz, 8 psi. The lower sequence shows mixing at a deflection rate of 100 Hz, and the pressure was 8 psi. The circulation flows are evident, as shown in the diagram at the center of the page.

FIG. 24A shows mixing time trends over a range of actuation times for water and water with glucose (600 g/L). FIG. 24B shows mixing time trends over a range of actuation pressures for water and light corn syrup.

VII. Applications and Extensions

It is anticipated that the devices of the invention will find particular use for as small scale culture vessels (e.g., tens to hundreds of microliters) for cells, e.g., bacteria, fungi, and/or other eukaryotic cells. Thus preferred embodiments of the devices address the needs for mixing and oxygenation that exist in this context. In this regard it is noted that the chambers may include a variety of additional components, e.g., pH or $O_2$ sensors (e.g., fluorescence-based sensors, chemical sensors), sensors for ions or various substrates such as glucose, waveguides to collect light, e.g., for spectroscopy, etc. (See, e.g., G. Liebsch, I. Klimant, C. Krause, O. S. Wolfbeis, "Fluorescent imaging of pH with optical sensors using time domain dual lifetime referencing," *Analytical Chemistry*, vol. 73, pp. 4354-4363, 2001; X. Lu, I. Manners, M. A. Winnik, "Polymer/silica composite films as luminescent oxygen sensors," *Macromolecules*, vol. 34, pp. 1917-1927, 2001; C. E. Miller, "Chemometrics for on-line spectroscopy applications—theory and practice," Journal of Chemometrics, vol. 14, pp. 513-528, 2000). The devices may be interfaced to equipment for collecting data from the sensors (e.g., computers such as PCs or work stations or any sort of microprocessor, spectrometers, etc.) to form an overall system for culturing cells and monitoring the culture.

The multichamber devices described herein offer the ability to conduct multiple fermentations (by which is meant culturing cells in general, not restricted as to cell type or culture conditions) under conditions of substantially identical oxygenation and mixing. This allows the comparison of multiple different cell strains in parallel. In addition, other parameters such as substrate concentrations, pH, etc., can be systematically varied. Thus the invention provides a method of selecting a strain that produces a desired product or degrades an unwanted compound comprising steps of (a) culturing a plurality of different strains, each in an individual chamber of a device of the invention; (b) measuring the amount of the desired or unwanted product in each of the chambers; and (c) selecting a strain that produces an optimum amount of a desired product or degrades a maximum amount of the unwanted compound. The invention further provides a method of selecting a bioprocess parameter comprising steps of (a) culturing an organism type in a plurality of chambers in a device of the invention, wherein the value of the bioprocess parameter varies within different chambers and wherein the organism produces a product or degrades a compound; (c) monitoring biomass in each of the chambers; and (d) identifying the value of the bioprocess parameter that results in optimum biomass, optimum product formation, or optimum compound degradation. Once optimal strains and/or parameters are selected using the devices of the invention, scale-up to larger vessels can be performed.

The devices of the invention may be used to culture essentially any type of cell including microorganisms such as bacteria (e.g., *eubacteria, archaebacteria*), filamentous or non-filamentous fungi (e.g., yeast), protozoa, and also plant cells, insect cells, mammalian cells, etc. Bacteria may be aerobes, facultative anaerobes, or anaerobes and include, but are not limited to, members of the following genera: *Escherichia, Enterobacter, Streptomyces, Azotobacter, Erwinia, Bacillus, Pseudomonas, Klebsiella, Proteus, Salmonella, Serratia, Shigella, Rhizobia, Rhodococcus, Vitreoscilla,* and *Paracoccus*. (See the Web sites with URLs www.bacterio.cict.fr/*eubacteria*.html and www.bacterio.cict.fr/archaea.html for lists of bacteria that may be used.). Yeast include, but are not limited to, members of the genera: *Saccharomyces, Schizosaccharomyces, Moniliella, Aureobasidium, Torulopsis, Candida, Trigonopsis, Trichosporon, Torulopsis, Zygosaccharomyces,* and *Yallowia*. Insect cells, e.g., cells that support the growth of baculovirus such as *Spodoptera frugiperda* sf9 cells (see, U.S. Pat. No. 4,745, 051) may be used. Such cells are particularly useful for production of recombinant proteins. Mammalian cells including, but not limited to, Chinese hamster ovary (CHO) cells, human embryonic kidney (HEK) cells, COS cells etc., may be used. In certain preferred embodiments of the methods the cells are of a type that is currently used in commercial bioprocesses.

The cells may be newly isolated or identified naturally occurring strains or variants, which may also be referred to as mutants. The cells may be selected, e.g., for a desirable phenotype. The cells may be genetically modified, e.g., using recombinant DNA technology. For example, cell or strain variants or mutants may be prepared by introducing appropriate nucleotide changes into the organism's DNA. The changes may include, for example, deletions, insertions, or substitutions of, nucleotides within a nucleic acid sequence of interest. The changes may also include introduction of a DNA sequence that is not naturally found in the strain or cell type, e.g, a sequence coding for a reporter molecule or a sequence coding for or providing a template for transcription of any molecule of interest. One of ordinary skill in the art will readily be able to select an appropriate method depending upon the particular cell type being modified. Methods for introducing such changes are well known in the art and include, for example, oligonucleotide-mediated mutagenesis, transposon mutagenesis, phage transduction, transformation, random mutagenesis (which may be induced by exposure to mutagenic compounds, radiation such as X-rays, UV light, etc.), PCR-mediated mutagenesis, DNA transfection, electroporation, etc.

One of ordinary skill in the art will be able to select appropriate culture media and environmental conditions for any particular cell type. Parameters such as oxygen delivery, temperature, and pH, etc., may be varied as appropriate. In addition, the microfermentor properties such as surface characteristics, vessel size, etc., may be modified depending upon the features of the particular cell type to be cultured. Parameters that may be varied (e.g., to identify optimum parameters) include, but are not limited to: growth medium (carbon/energy source (e.g., glycerol, succinate, lactate, and sugars such as, e.g., glucose, lactose, sucrose, and fructose), nitrogen source, precursors, and nutrients such as vitamins and minerals, salts, etc.), temperature, pH, redox potential, mixing rate, ionic strength, osmotic pressure, water activity, hydrostatic pressure, concentration of inducers and repressors, etc. Any of these parameters may be varied in different ways in individual chambers operating in parallel. In addition, the devices can be used to screen for compounds that have particular effects on cells, e.g., in screening for pharmaceutical agents, evaluating the effects of potential toxins, etc.

Although the discussion herein has focused on delivering $O_2$ to a chamber, it will be appreciated that by appropriate choice of material removal of gas(es) such as $CO_2$ from the chamber by diffusion across the membrane can also be achieved, provided that the concentration of such gas(es) in the reservoir is maintained below that in the chamber. Thus in order to maintain a concentration of a certain gas below a given value, the concentration of that gas in the hollow space should be below that given value. It will be appreciated that the same principle applies to the addition and/or removal of any molecule for which a suitable permeably membrane exists. Thus the invention is useful to provide small molecules such as substrates and nutrients, ions, etc., to the interior of the chamber and to remove such molecules. The invention therefore is useful in the bioprocess context for pH control and substrate feed and removal of waste products in addition to mixing and oxygenation.

More generally, the invention may be used in any of a variety of applications involving chemical reactions, in which mixing and supplying reagents and/or removal of products is desired, e.g. "lab-on-a-chip" (Figeys, D., and Pinto, D., *Anal. Chem.* 72A:330-35, 2000), micrototal analysis systems (μTAS) (Jakeway, S., et al., *Fresenius J. Anal. Chem.* 336:525-39, 2000; Ransey, J., van den Berg, A., (eds.) *Micro Total Analysis Systems* 2001. Boston: Kluwer Acad. 2001), etc. It is noted that the invention may also provide for heat exchange, by appropriately cooling or heating the gas or fluid in the hollow cavities. While the invention is likely to be most useful for applications involving the mixing of small volumes, it is not limited to that.

The foregoing description is to be understood as being representative only and is not intended to be limiting. Alternative systems and techniques for making and using the compositions and devices of the invention and for practicing the inventive methods will be apparent to one of skill in the art and are intended to be included within the accompanying claims.

I claim:

1. A device for fluid mixing and gas exchange comprising: a housing defining an enclosed chamber for holding a liquid, wherein at least 1 wall of the chamber comprises a plurality of gas-permeable portions, wherein the volume of the chamber is between approximately 0.5 μl, and approximately 10 ml, and wherein the gas-permeable portions are selectively deflectable into the interior of the chamber.

2. The device of claim 1, wherein 1 wall comprises a plurality of gas-permeable portions.

3. The device of claim 1, wherein 2 walls comprise a plurality of gas-permeable portions.

4. The device of claim 1, wherein at least 2 walls comprise a plurality of gas-permeable portions.

5. The device of claim 1, wherein at least one wall of the chamber comprises at least 3 selectively deflectable gas-permeable portions.

6. The device of claim 1, wherein at least one wall of the chamber comprises at least 4 selectively deflectable gas-permeable portions.

7. The device of claim 1, wherein at least one wall of the chamber comprises at least 5 selectively deflectable gas-permeable portions.

8. The device of claim 1, wherein at least one wall of the chamber comprises at least 6 selectively deflectable gas-permeable portions.

9. The device of claim 1, wherein at least one wall of the chamber comprises between 6 and 10 selectively deflectable gas-permeable portions.

10. The device of claim 1, wherein at least one wall of the chamber comprises at least 10 selectively deflectable gas-permeable portions.

11. The device of claim 1, wherein the total area of the selectively deflectable portions is at least 25% of the area of the wall that comprises them.

12. The device of claim 1, wherein the total area of the selectively deflectable portions is at least 50% of the area of the wall that comprises them.

13. The device of claim 1, wherein the total area of the selectively deflectable portions is at least 75% of the area of the wall that comprises them.

14. The device of claim 1, wherein the selectively deflectable portions are spaced apart.

15. The device of claim 1, wherein the selectively deflectable portions are separated by non-deflectable portions of the wall.

16. The device of claim 1, wherein the selectively deflectable portions are substantially parallel to one another.

17. The device of claim 1, wherein the selectively deflectable portions have uniform widths in the plane of the wall that comprises them.

18. The device of claim 1, wherein at least one selectively deflectable portion has a nonuniform width in the plane of the wall that comprises the selectively deflectable portion.

19. The device of claim 18, wherein adjacent deflectable portions comprise complementary convex and concave regions.

20. The device of claim 1, wherein the volume of the chamber is at least 0.5 μl.

21. The device of claim 1, wherein the volume of the chamber is between 0.5 μl and 10 μl.

22. The device of claim 1, wherein the vohnne of the chamber is between 10 μl and 50 μl.

23. The device of claim 1, wherein the volume of the chamber is between 50 μl and 150 μl.

24. The device of claim 1, wherein the volume of the chamber is between 150 μl and 500 μl.

25. The device of claim 1, wherein the volume of the chamber is between 500 μl and 1 μl.

26. The device of claim 1, wherein the chamber is macroscopic.

27. The device of claim 1, wherein the ratio of the area of the wall of the chamber comprising deflectable portions to the volume of the chamber is at least 50/m.

28. The device of claim 1, wherein the ratio of the area of the wall of the chamber comprising deflectable portions to the volume of the chamber is between 50/m and 20,000/m.

29. The device of claim 1, wherein the ratio of the area of the wall of the chamber comprising deflectable portions to the volume of the chamber is between 100/m and 10,000/m.

30. The device of claim 1, wherein a deflectable portion is constrained so that it does not move along its perimeter when actuated.

31. The device of claim 1, wherein the deflectable portions are independently deflectable.

32. The device of claim 1, wherein at least some of the deflectable portions are not independently deflectable.

33. The device of claim 1, wherein at least some of the deflectable portions are deflectable in groups.

34. The device of claim 33, wherein the deflectable portions in a group deflect at the same time.

35. The device of claim 33, wherein the deflectable portions in a group deflect at different times.

36. The device of claim 1, wherein the deflectable portions form part of a continuous gas-penneable layer of material.

37. The device of claim 1, wherein the thickness of the deflectable portions is between 1-1000 μm.

38. The device of claim 1, wherein the thickness of the deflectable portions is between 5-500 μm.

39. The device of claim 1, wherein the thickness of the deflectable portions is between and 100-300 μm.

40. The device of claim 1, wherein the gas-permeable deflectable portions are deflectable at a rate between 1-1,000 Hz.

41. The device of claim 1, wherein the gas-permeable deflectable portions are deflectable at a rate between 10-500 Hz.

42. The device of claim 1, wherein the gas-permeable deflectable portions are deflectable at a rate between 25-200 Hz.

43. The device of claim 1, wherein the gas-permeable deflectable portions are permeable to oxygen.

44. The device of claim 1, wherein the gas-permeable deflectable portions have a diffusivity for $O_2$ greater than $1.0 \times 10^{-5}$ cm$^2$/s.

45. The device of claim 1, wherein the gas-permeable deflectable portions have a diffusivity for $O_2$ greater than $2.0 \times 10^{-5}$ cm$^2$/s.

46. The device of claim 1, wherein the gas-permeable deflectable portions have a diffusivity for $O_2$ greater than $3.0 \times 10^{-5}$ cm$^2$/s.

47. The device of claim 1, wherein the gas-permeable detlectable portions are made of a material in which the solubility of $O_2$ is greater than $5 \times 10^{-3}$ mol/Liter for air at 1 atm.

48. The device of claim 1, wherein the gas-permeable detlectable portions are made of a material in which the solubility of $O_2$ is greater than $1.0 \times 10^{-3}$ mol/Liter for air at 1 atm.

49. The device of claim 1, wherein the gas-permeable deflectable portions have a permeability to $O_2$ of between 750 and 850 Barrer.

50. The device of claim 1, wherein the gas-permeable deflectable portions have a permeability to $O_2$ of between 850 and 1000 Barrer.

51. The device of claim 1, wherein the gas-permeable deflectable portions have a permeability to $O_2$ of between 400 and 750 Barrer.

52. The device of claim 1, wherein the gas-permeable deflectable portions have a permeability to $O_2$ of less than 400 Barrer.

53. The device of claim 1, wherein the gas-permeable deflectable portions are permeable to $CO_2$.

54. The device of claim 1, wherein the deflectable portions comprise an elastomeric material.

55. The device of claim 54, wherein the elastomeric material is PDMS.

56. The device of claims 1, 36, or 54 wherein the housing and the deflectable portions comprise different materials.

57. The device of claims 1, 36, or 54, wherein the housing and the deflectable portions comprise the same material.

58. The device of claims 1, 36, or 54, wherein the housing and the deflectable portions comprise an elastomeric material.

59. The device of claim 58, wherein the elastomeric material is PDMS.

60. The device of claim 1, wherein at least a portion of the housing is made of a material selected from the group consisting of: glass, plastic, or metal.

61. The device of claim 1, further comprising a substrate, wherein the housing is positioned on the substrate.

62. The device of claim 61, wherein the substrate forms a wall of the chamber.

63. The device of claim 1, each portion is deflectable by pressurizing a cavity in communication with the deflectable portion or by pressurizing a cavity in communication with a different deflectable portion.

64. The device of claim 1, wherein at least one deflectable portion is deflectable by pressurizing a cavity in communication with a different deflectable portion.

65. The device of claim 1, wherein each deflectable portion is in communication with a cavity.

66. The device of claim 65, wherein the cavities are not connected with one another.

67. The device of claim 63, wherein at least two of the cavities are connected with one another via a hollow region that has a substantially smaller cross-sectional area thah the area of either cavity so that pressurization of a first cavity results in deflection of a deflectable portion in communication with the second cavity.

68. The device of claim 63, wherein the cavities are pressurized using a gas from a high pressure reservoir.

69. The device of claim 68, wherein the gas is humidified.

70. The device of claim 63, wherein the cavities are pressurized at a pressure ranging from 1-200 psi.

71. The device of claim 63, wherein the cavities are pressurized at a pressure ranging from 1-30 psi.

72. The device of claim 63, wherein the cavities comprise an assembly of tubes that are blind at one or both ends, and wherein at least some of the tubes are connected to a high pressure reservoir.

73. The device of claim 63, wherein the cavities comprise an assembly of tubes that are blind at one or both ends, and wherein each of the tubes is connected to a high pressure reservoir.

74. The device of claim 63, wherein the cavities comprise an assembly of tubes that are blind at one or both ends, wherein at least one of the tubes is connected to a high pressure reservoir, and wherein the remaining tubes are interconnected with at least one other tube.

75. The device of claims 72, 73, or 74, wherein the connection to a high pressure reservoir is via a valve that controls pressurization of the tube.

76. The device of claim 63, wherein the cavities comprise an assembly of tubes, wherein at least one of the tubes connected to a high pressure reservoir, and wherein at least one of the tubes is connected to the atmosphere or to a low pressure reservoir at lower pressure than that of the high pressure reservoir.

77. The device of claim 63, wherein the cavities comprise an assembly of tubes, wherein at least one of the tubes is connected to a high pressure reservoir, and wherein at least one of the tubes is connected to the atmosphere or to a low pressure reservoir at lower pressure than the high pressure reservoir, and wherein the remaining tubes are interconnected with at least one other tube.

78. A device for fluid mixing and gas exchange comprising:

a housing defining a chamber for holding a liquid, wherein at least 1 wall of the chamber comprises a plurality of gas-permeable portions, wherein the gas-permeable portions are selectively deflectable into the interior of the chamber by pressurizing a cavity in communication with the deflectable portion or by pressurizing a cavity in communication with a different deflectable portion, and wherein the cavity comprises an assembly of tubes, wherein at least one of the tubes is connected to a high pressure reservoir, and wherein at least one of the tubes is connected to the atmosphere or to a low pressure reservoir at lower pressure than that of the high pressure reservoir.

79. A device for fluid mixing and gas exchange comprising:

a housing defining a chamber for holding a liquid, wherein at least 1 wall of the chamber comprises a plurality of gas-permeable portions, wherein the gas-permeable portions are selectively deflectable into the interior of the chamber by pressurizing a cavity in communication with the deflectable portion or by pressurizing a cavity in communication with a different deflectable portion, and wherein the cavity comprises an assembly of tubes, wherein at least one of the tubes is connected to a high pressure reservoir, wherein at least one of the tubes is connected to the atmosphere or to a low pressure reservoir at lower pressure than the high pressure reservoir, and wherein the remaining tubes are interconnected with at least one other tube.

80. The device of claim 63, wherein the cavities are located within the housing.

81. The device of claim 63, wherein a deflectable portion separates a cavity from the interior of the chamber.

82. The device of claim 63, wherein at least some of the cavities are connected to an actuation interface port.

83. The device of claim 82, further comprising connecting means for connecting the actuation interface port to a high pressure reservoir or a low pressure reservoir.

84. The device of claim 82, further comprising an array of valves for controlling flow from the high pressure reservoir into the cavities or from the cavities to a low pressure reservoir or the atmosphere.

85. The device of claim 84, further comprising a manifold that interfaces the array of valves with the cavities.

86. The device of claim 1, wherein the chamber has at least one access port allowing introduction of fluid into the chamber or removal of fluid from the chamber.

87. The device of claim 1, wherein the chamber has at least two access ports allowing introduction of fluid into the chamber or removal of fluid from the chamber.

88. The device of claim 1, wherein the chamber has at least four access ports allowing introduction of fluid into the chamber or removal of fluid from the chamber.

89. The device of claim 1, further comprising a high pressure reservoir.

90. The device of claim 89, wherein the high pressure reservoir is filled with gas having a higher oxygen concentration than that in ambient air at standard temperature and pressure.

91. The device of claim 89, wherein the gas is humidified.

92. The device of claim 1, further comprising a low pressure reservoir.

93. The device of claim 1, further comprising a computer.

94. The device of claim 1, further comprising means for sensing a parameter selected from the group consisting of: pH, dissolved oxygen, optical density, substrate concentration, and product concentration.

95. The device of claim 94, wherein the sensing means comprises a fluorescence-based detector.

96. The device of claim 94, wherein the sensing means comprises a chemical detector.

97. The device of claim 94, wherein the sensing means is located within the chamber.

98. The device of claim 1, wherein the device comprises a plurality of chambers having selectively deflecrable gas-permeable portions.

99. The device of claim 98, wherein each portion is deflectable by pressurizing a cavity in communication with the deflectable portion or by pressurizing a cavity in communication with a different deflectable portion.

100. The device of claim 99, wherein the cavities extend across multiple chambers so that pressurization of a single cavity results in deflection of a deflectable portion into each of the multiple chambers.

101. The device of claim 99, wherein the chambers and cavities comprise layers within an elastomeric block.

102. The device of claim 99, wherein the cavities comprise an assembly of tubes that are blind at one or both ends and that are connected either to a high pressure reservoir, a low pressure reservoir, to another tube, or to a combination of the foregoing.

103. A device comprising a set of tubes made at least in part of a gas-permeable material, wherein the tubes form portions of a wall of an enclosed chamber, wherein the volume of the chamber is between approximately 0.5 μl, and approximately 10 ml, and wherein the portions of the wall are selectively deflectable into the interior of the chamber.

104. A device comprising a set of tubes made at least in part of a gas-permeable material, wherein the tubes are separated from the interior of an enclosed chamber by a layer of gas-permeable material that forms a wall of the chamber, wherein the tubes are selectively pressurizable, and wherein pressurization of the tubes causes portions of the wall to deflect into the interior of the chamber.

105. A method of achieving mixing and gas exchange of a volume of liquid comprising the steps of:
 (i) introducing a liquid into the chamber of the device of claim 1; and
 (ii) actuating the device so as to repetitively deflect the deflectable gas-permeable portions into the chamber.

106. A method of achieving mixing and gas exchange in a volume of liquid comprising the steps of:
 (i) introducing the liquid into die chamber of the device of claim 63; and
 (ii) actuating the device so as to repetitively deflect the deflectable gas-permeable portions into the chamber, wherein deflection is accomplished by pressurizing the cavities.

107. The method of claim 105 or 106, wherein the gas-permeable portions are deflected in a sequence that produces peristaltic action.

108. The method of claim 105 or 106, wherein mixing of two initially unmixed liquids is essentially complete within 1 minute of actuation.

109. The method of claim 105 or 106, wherein mixing of two initially unmixed liquids is essentially complete within about 10 seconds of actuation.

110. The device of claim 78 or 79, wherein the connection to the atmosphere or to a low pressure reservoir is via a valve that controls flow of gas through the tube.

111. The device of claim 78 or 79, wherein the cavities are connected at one end to a high pressure reservoir and at the other end to a valve which can be vented to the atmosphere or to a low pressure reservoir so that when a valve is closed, the corresponding cavity is pressurized, resulting in deflection, and when the valve is opened, gas flows through the cavity and the cavity is depressurized.

* * * * *